United States Patent [19]

Fuchs et al.

[11] Patent Number: 5,250,515
[45] Date of Patent: Oct. 5, 1993

[54] METHOD FOR IMPROVING THE EFFICACY OF INSECT TOXINS

[75] Inventors: Roy L. Fuchs, St. Charles; Ganesh M. Kishore, Chesterfield; Susan C. MacIntosh, St. Louis, all of Mo.

[73] Assignee: Monsanto Company, St. Louis, Mo.

[21] Appl. No.: 812,890

[22] Filed: Dec. 20, 1991

Related U.S. Application Data

[63] Continuation of Ser. No. 179,709, Apr. 11, 1988, abandoned.

[51] Int. Cl.$^5$ .................... A01N 27/00; C07K 13/00; C07K 15/00; A61K 35/78
[52] U.S. Cl. .................... 514/12; 424/93 L; 424/195.1; 530/370; 530/379
[58] Field of Search .................... 47/58; 530/350, 370, 530/379; 514/12; 424/93 L, 195.1

[56] References Cited

U.S. PATENT DOCUMENTS 4,016,265  4/1977  Inoue et al. .................... 514/85

FOREIGN PATENT DOCUMENTS

WO87/03303  6/1987  World Int. Prop. O. .

OTHER PUBLICATIONS

Hilder, et al. (1987) Nature 330: 160–163.
Klausner (1984) Bio/Technology 2: 408–419.
Yu, et al. (1987) J. Gen. Appl. Microbiol. 33: 459–462.
Hofte, et al. (Jun. 1989) Microbiological Reviews 53 (2): 242–255.
Wagner, et al. (1967) Arch. Biochem. Biophys. 121: 672–677.
Griffiths (1984) J. Sci. Food Agric. 35: 481–486.
John S. Graham et al., Wound-Induced Proteinase Inhibitors from Tomato Leases, *Journal of Biol. Chem.* (1985) vol. 260, No. 11, pp. 6555–6560.
J. Sanchez-Serrano et al., Nucleotide Sequence of Proteinase Inhibitor II Encoding cDNA of Potato (*Solanum tuberosum*) and Its Mode of Expression, *Mol. Gen. Genet* (1986) 203:15–20.
Martin S. Williams et al., Nucleotide Sequence of Barley Chymotrypsin Inhibitor-2 (CI-2) and Its Expression in Normal and High-Lysine Barley, *Eur. J. Biochem.* (1987) 165:99–106.
Leslie M. Hoffman et al., Structure of Soybean Kunitz Trypsin Inhibitor mRNA Determined from cDNA by Using Oligodeoxynucleotide Primers, *Plant Molecular Biology* (1984) 3:111–117.
R. H. Shukle et al., Lipoxygenase, Trypsin Inhibitor, and Lectin from Soybeans: Effects on Sphingidae), *Environ. Entomol.* (1983) 12:787–791.
Iordanka Kourteva et al., Assay for Enzyme Inhibition: Detection of Natural Inhibitors of Trypsin and Chymotrypsin, *Analytical Biochemistry* (1987) 162:345–349.
Rosemarie W. Hammond et al., Molecular Cloning and Analysis of a Gene Coding for the Bowman-Birk Protease Inhibitor in Soybean, *The Journal of Biological Chemistry* (1984) 25:9883–9890.
Angharad M. R. Gatehouse et al., Isolation and Characterization of Trypsin Inhibitors from Cowpea (*Vigna unguiculata*), *Phytochemistry* (1980) 19:751–756.
Angharad M. R. Gatehouse et al., Biochemical Basis of Insect Resistance in (*Vigna unquiculata*), *J. Sci. Food Agric.* (1979) 30:948–958.
C. A. Ryan et al., Proteinase Inhibitors in Natural Plant Protection, *Phytochemistry* (1974) 8:123–140.
Charles P. Moran, Jr. et al., Nucleotide Sequences that Signal the Initiation of Transcription and Translation in *Bacillus subtilis*, *Mol. Gen. Genet* (1982) 186:339–346.

(List continued on next page.)

*Primary Examiner*—Che S. Chereskin
*Attorney, Agent, or Firm*—Dennis R. Hoerner, Jr.; Howard C. Stanley

[57] ABSTRACT

A method for potentiating the insecticidal activity of a protein toxin of *Bacillus thuringiensis* bacteria is disclosed. A potentiating amount of trypsin inhibitor is co-administered to the insect along with the toxin. Improved insecticidal compositions are also disclosed which contain an insecticidal amount of a protein toxin of *Bacillus thuringiensis* and a potentiating amount of a trypsin inhibitor.

4 Claims, 16 Drawing Sheets

OTHER PUBLICATIONS

Charles P. Moran, Jr. et al., Anatomy of a Sporulation Gene: Nucleotide Sequences that Signal the Initiation of Transcription and Translation, *Molecular Cloning and Gene Regulation in Bacilli* (eds. Ganessan, A. T., Chang, S. Hoch, J. A. (1982) 325-333.

Corinna Herrnstadt et al., A New Strain of *Bacillus thuringiensis* with Activity against Coleopteran Insects, *Biotechnology* (1986) 4:305-308.

Akihiko Tojo et al., Dissolution and Degradation of *Bacillus thuringiensis* β-Endotoxin by Gut Juice Protease of the Silkworm *Bombyx mori, Applied and Environmental Microbiology* (1983) 45:576-580.

John H. Schesser et al., Bioassay for Homogeneous Parasporal Crystal of *Bacillus thuringiensis* Using the Tobacco Hornworm, *Manduca sexta, Applied and Environmental, Microbiology* (1977) 33:878-880.

Donovan E. Johnson et al., Incidence of Insect Cell Cytolytic Activity among *Bacillus thuringiensis* Serotypes, *FEMS Microbiology Letters* (1987) 43:121-125.

Sylvia A. McPherson et al., Characterization of the Coleopteran Specific Protein Gene of *Bacillus thuringiensis var. tenebrionis, Bio/Technology* (1988) 6:61-66.

Vaughan A. Hilder et al., A Novel Mechanism of Insect Resistance Engineered into Tabacco, *Nature* (1987) 330:160-163.

Shin-Ichi Ishii et al., Immobilized Anhydrotrypsin as a Specific Affinity Adsorbent for Tryptic Peptides, *Methods in Enzymology* (1983) 91:378-383.

Louise Slade Gennis et al., Double-headed Protease Inhibitors from Black-eyed Peas, *The Journal of Biological Chemistry* (1976) 251:734-740.

Michael Elfant et al., Isolation and Characterization of a Proteinase Inhibitor from Marama Beans (42184), *Proceedings of the Society for Experimental Biology and Medicine* (1985) 329-333.

David L. R. Hwang et al., Purification, Partial Characterization, and Immunological Relationships of Multiple Low Molecular Weight Protease Inhibitors of Soybean, *Biochimmica et Biophysica Acta.* (1977) 495:369-382.

Takashi Yamamoto et al., Two Types of Entomocidal Toxins in the Parasporal Crystals of *Bacillus thuringiensis kurstaki, Archives of Biochemistry and Biophysics* (1983) 227:233-241.

A. E. M. Hassan et al., The Effect of Dimilin on the Ultrastructure of the Integument of *Manduca sexta, J. Insect Physiol.* (1987) 33:669-676.

David R. Wilcox et al., Genetic Engineering of Bioinsecticides, *Protein Engineering* (1986) 395-393.

Bruno Baumgartner et al., Partial Characterization of a Protease Inhibitor which Inhibits the Major Endopeptidase Present in the Cotyledons of Mung Beans, *Plant Physiol.* (1976) 58:1-6.

M. Kunitz, Crystalline Soybean Trypsin Inhibitor, *J. Gen. Physiol.* (1946) 29:149.

Charles A. McWherter et al., Novel Inhibitors of Human Leukocyte Elastase and Cathepsin G. Sequence Variants of Squash Seed Protease Inhibitor with Altered Protease Selectivity, *Biochemistry* (1989) 28:5708.

Yehudith Birk et al., Effect of Soybean Trypsin Inhibitors on the Development and Midgut Proteolytic activity of Tribolium castaneum Larvae, *Entymologia* (1960) 22:318-326.

A. Krieg et al., *Bacillus thuringiensis var. tenebrionis*, a New Pathotype Effective against LarVae of Coleoptera, Translated from German by Chem-Info Services, Inc.; (1984).

C. A. Ryan, Proteinase Inhibitors, *The Biochemistry of Plants* (1981) 6:351-370.

Michael Laskowski, Jr. et al., Protein Inhibitors of Proteinases, *Ann. Rev. Biochem.* (1980) 49:593-626.

| | | |
|---|---|---|
| 1 | ASP-PHE-VAL-LEU-ASP-ASN-GLU-GLY-ASN-PRO- | 10 |
| 11 | LEU-GLU-ASN-GLY-GLY-THR-TYR-TYR-ILE-LEU- | 20 |
| 21 | SER-ASP-ILE-THR-ALA-PHE-GLY-GLY-ILE-ARG- | 30 |
| 31 | ALA-ALA-PRO-THR-GLY-ASN-GLU-ARG-CYS-PRO- | 40 |
| 41 | LEU-THR-VAL-VAL-GLN-SER-ARG-ASN-GLU-LEU- | 50 |
| 51 | ASP-LYS-GLY-ILE-GLY-THR-ILE-ILE-SER-PRO- | 60 |
| 61 | SER-TYR-ARG-ILE-ARG-PHE-ILE-ALA-GLU-GLY- | 70 |
| 71 | HIS-PRO-LEU-SER-LEU-LYS-PHE-ASP-SER-PHE- | 80 |
| 81 | ALA-VAL-ILE-MET-LEU-CYS-VAL-GLY-ILE-PRO- | 90 |
| 91 | THR-GLU-TRP-SER-VAL-VAL-GLU-ASP-LEU-PRO- | 100 |
| 101 | GLU-GLY-PRO-ALA-VAL-LYS-ILE-GLY-GLU-ASN- | 110 |
| 111 | LYS-ASP-ALA-MET-ASP-GLY-TRP-PHE-ARG-LEU- | 120 |
| 121 | GLU-ARG-VAL-SER-ASP-ASP-GLU-PHE-ASN-ASN- | 130 |
| 131 | TYR-LYS-LEU-VAL-PHE-CYS-PRO-GLN-GLN-ALA- | 140 |
| 141 | GLU-ASP-ASP-LYS-CYS-GLY-ASP-ILE-GLY-ILE- | 150 |
| 151 | SER-ILE-ASP-ASP-ASP-GLY-HIS-THR-ARG-ARG- | 160 |
| 161 | LEU-VAL-VAL-SER-LYS-ASN-LYS-PRO-LEU-VAL- | 170 |
| 171 | VAL-GLN-PHE-GLN-LYS-LEU-ASP-LYS-GLU-SER- | 180 |
| 181 | LEU. | |

POTENTIATION of B.t.t. TOXICITY with SOYBEAN KUNITZ INHIBITOR
Colorado potato beetle, leaf assay

TOBACCO BUDWORM
LARVAL WEIGHT REDUCTION ASSAY

FIGURE 10

CRUDE SEED EXTRACTS
Potentiation effect with B.t. Toxin Proteins

FIGURE 11

| | | |
|---|---|---|
| 5' - | AAGCTTGCAT GCCTGCAGGT CCGATG*[TGAG ACTTTTCAAC AAAGGGTAAT | 50 |
| | ATCCGGAAAC CTCCTCGGAT TCCATTGCCC AGCTATCTGT CACTTTATTG | 100 |
| | TGAAGATAGT GGAAAAGGAA GGTGGCTCCT ACAAATGCCA TCATTGCGAT | 150 |
| | AAAGGAAAGG CCATCGTTGA AGATGCCTCT GCCGACAGTG GTCCCAAAGA | 200 |
| | TGGACCCCCA CCCACGAGGA GCATCGTGGA AAAAGAAGAC GTTCCAACCA | 250 |
| | CGTCTTCAAA GCAAGTGGAT TGATGTGAT]G GTCCGATG[TG AGACTTTTCA | 300 |
| | ACAAAGGGTA ATATCCGGAA ACCTCCTCGG ATTCCATTGC CCAGCTATCT | 350 |
| | GTCACTTTAT TGTGAAGATA GTGGAAAAGG AAGGTGGCTC CTACAAATGC | 400 |
| | CATCATTGCG ATAAAGGAAA GGCCATCGTT GAAGATGCCT CTGCCGACAG | 450 |
| | TGGTCCCAAA GATGGACCCC CACCCACGAG GAGCATCGTG GAAAAGAAG | 500 |
| | ACGTTCCAAC CACGTCTTCA AGCAAGTGG ATTGATGTGA T]ATCTCCACT | 550 |
| | GACGTAAGGG ATGACGCACA ATCCCACTAT CCTTCGCAAG ACCCTTCCTC | 600 |
| | TATATAAGGA ACTTCATTTC ATTTGGAGAG GACACGCTGA CAAGCTGACT | 650 |
| | CTAGCAGATC T - 3' | 661 |

FIGURE 14

METHOD FOR IMPROVING THE EFFICACY OF INSECT TOXINS

This is a continuation of application Ser. No. 07/179,709, filed Apr. 11, 1988, now abandoned.

The present invention relates to insect toxins produced by strains of *Bacillus thuringiensis*. More particularly, the present invention relates to a method for improving the efficacy of such toxins by co-administering an effective amount of a trypsin inhibitor.

Protease inhibitors are found in multiple forms in various tissues of plants, animals, insects and microorganisms. Serine protease inhibitors are well characterized and typically function by a common mechanism. Each inhibitor contains an active site, a surface peptide bond which serves as a substrate for the enzyme forming a very stable enzyme-inhibitor complex. Several families of serine protease inhibitors have been identified. Kunitz and Bowman-Birk type trypsin inhibitors are commonly found in plant species. These inhibitors are commonly found in seeds and tubers of the legume family (Leguminosae). The physiological functions of protease inhibitors in plants have been questioned for many years. Inhibitors in storage organs may have regulatory or protective roles in controlling proteases before or during germination, Ryan, C. A., (1981) *The Biochemistry of Plants*, Vol. 6, p.364. Inhibitors may inhibit endogenous proteases that might be accidentally released from ruptured protein bodies thereby protecting cytoplasmic proteins from digestion; Baumgartner, et al. (1976) *Plant Physiol.* 58, 1. Protease inhibitors may function by inhibiting activation of zymogens (e.g. chitin synthase, Hassan et al., 1987 *J. Insect Physiol.* 33(9) pp. 669-676). Plant protease inhibitors may also have evolved as a mechanism against plant pests. Several groups have studied the effects of feeding plant protease inhibitors to insect larvae and found that some inhibitors are insecticidal at high levels. However, it is important to note that an insecticidal effect is observed only at inhibitor concentrations of 2 to 5 wt % of the total diet; Gatehouse, et al., (1983) *J. Sci. Food Agric.* 34:345-350.

In the late 1970's a variety of cowpea (*Vigna unguiculata* TVu2027) was selected from over five thousand cowpea varieties for its resistance toward the larvae of bruchid beetle (*Callosobuchas maculatus*), a major storage pest in West Africa. Biochemical studies suggested that elevated levels of trypsin inhibitor within the seeds are responsible for the insect tolerance (U.S. Pat. No. 4,640,836). When purified cowpea trypsin inhibitor (CPTI) was mixed with cowpea meal from an insect sensitive variety at levels of 1.5 to 10.0% (w/w) the development of the beetle was greatly reduced and significant mortality was observed, Gatehouse, et al. (1983) *J. Sci. Food Agric.* 34:345-350. Transgenic plants have recently been genetically engineered which expressed the cowpea trypsin inhibitor and exhibit enhanced insect tolerance. Plants having the highest content of CPTI (1% of soluble protein) exhibited the highest trypsin inhibitory activity and also produced the highest levels of insect mortality; Hilder, et al. (1987) *Nature* 330:160-163.

A totally distinct class of proteins have been isolated from numerous strains of *Bacillus thuringiensis* (B.t.) which also inhibit insect development and have insecticidal activity. The proteincrystalline toxins produced by B.t. represent the major class of proteins used for insect control; Klausner, *Bio/Technology* 2:408-419. B.t. is a gram-positive, spore forming, soil bacterium which characteristically produces a parasporal crystal protein which accounts for the insecticidal activity. A variety of B.t. strains have been isolated which produce toxins active against a wide range of insects including Lepidopterans, Coleopterans and Dipterans. Numerous Lepidopteran-active strains of B.t. have been isolated and the parasporal crystal proteins analyzed. These proteins are typically encoded as 130 to 140 Kd proteins which are subsequently proteolytically activated in the midgut of the susceptible insect to form the active toxin having a molecular eight of about 65-70 Kd, Aronson, et al., (1968) *Microbiol. Rev.* 50: 1-24. Crystal/spore preparations of B.t. subspecies *kurstaki* have been used as commercial insecticides for many years in products such as DIPEL® (Abbott Laboratories) and THURICIDE® (Sandoz). These commercial B.t.k. insecticides are effective against more than fifty species of Lepidopteran pests, Wilcox, et al. (1986) *Protein Engineering*, Inouye and Sarma (Eds.) *Academic Press*, NY. The toxin produced by B.t. *israeliensis*, isolated in Israel in 1977, has been demonstrated to be toxic to larvae of several Dipteran aquatic insects such as mosquitoes and black flies (EPO Publ. No. 0195285). Recently, B.t. toxins were isolated from B.t. *tenebrionis* and B.t. *san diego* which exhibit toxicity against Coleopteran insects; see Herrnstadt et al., 1986, *Bio/Technology* 4:305-308 and Krieg, et al., 1983, *Z. Angew. Entomologie* 500-508.

Agronomically important insects include, but are not limited to, *Heliothis virescens* (tobacco budworm), *Manduca sexta* (tobacco hornworm), *Heliothis zea* (corn earworm or cotton bolworm), *Agrotis ipsilon* (black cutworm), *Ostrinia nubilalis* (European cornborer), *Trichoplusia ni* (T.ni) (Cabbage looper), *Anticarsia gemmatalis* (velvetbean caterpillar), *Spodoptera exigua* (beet armyworm).

BRIEF DESCRIPTION OF DRAWINGS

FIG. 1 shows the complete amino acid sequence for the Kunitz-type trypsin inhibitor of soybean.

FIG. 9 illustrates the potentiation of B.t.k. by the Kunitz-type trypsin inhibitor of soybean.

FIG. 10 illustrates a standard curve for tobacco budworm larval weight reduction due to exposure to B.t.k. toxin protein.

FIG. 11 illustrates the potentiation of the biological activity of B.t. toxins by crude seed extracts containing trypsin inhibitors.

FIG. 14 shows the DNA sequence for the enhanced CaMV35S promoter.

STATEMENT OF THE INVENTION

Figure 2:
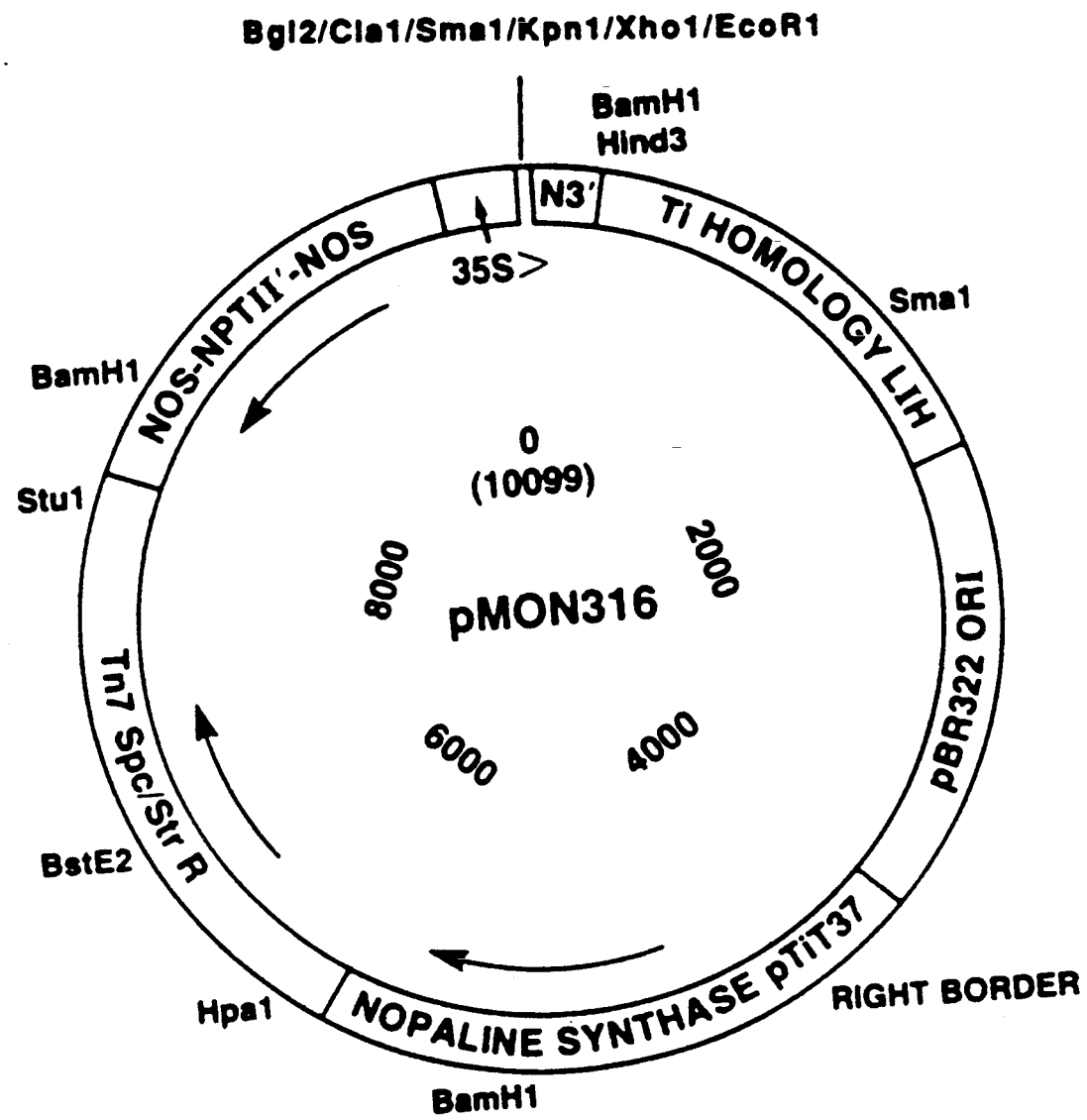
FIG. 2 shows a plasmid map for plant transformation vector cassette pMON316.

In its broadest aspect, the present invention provides a method for enhancing the insecticidal activity of the parasporal protein of the soil bacterium *Bacillus thuringiensis*. More particularly, the insecticidal activity of a B.t. toxin is improved by co-administering an effective amount of a trypsin inhibitor. By "insecticidally effective amount" is meant that amount of toxin necessary to cause insect mortality or larval weight reduction and/or delay in development.

It has been found that extremely low levels of trypsin inhibitor, levels which alone exhibit no insecticidal activity, strongly potentiate the insecticidal activity of B.t. toxins toward their target insects. Typically, the addition of purified trypsin inhibitor to a level of at least 0.0002% of inhibitor wt/wt of diet increases the mortality observed with B.t. toxin alone by two to five fold, when the B.t. toxin concentration used causes minimal (~10%) mortality. The inhibitor/diet ratio is preferably between about 0.000002 and 2.0% wt/wt and more preferably between about 0.00002 and 0.02% wt/wt.

Therefore, in one aspect the present invention provides improved toxin compositions comprising an insecticidally effective amount of a toxin protein of a *Bacillus thuringiensis* and an effective amount of trypsin inhibitor to enhance the insecticidal activity of the B.t. toxin. The inhibitor is present in a molar ratio versus toxin between $1/10^{-2}$ to $10^6/1$ when the toxin is present at a concentration between and $10^{-10}$ and $10^{-7}$ M. An inhibitor/toxin ratio between about 1/1 and $10^4/1$ is preferred. Those skilled in the art recognize that the potentiating effect due to the presence of inhibitor will vary with the target insect.

In another aspect, the present invention provides a means to enhance the insecticidal resistance of plants which express a B.t. toxin by engineering the transgenic plants to also express a trypsin inhibitor.

In yet another aspect, the present invention provides a means to enhance the effectiveness of plant colonizing bacteria which have been transformed to express the toxin of B.t. by transforming the bacteria to also express the inhibitor. The plant colonizing bacteria may either associate with the plant on the surface of the plant (leaf or roots) or may actually reside within the plant. Such bacteria are described in EP Publication Numbers 185,005 and 200,708 as well as PCT Publication No. WO 87/03303.

Lepidopteran-type toxins and structural genes encoding such toxins can be obtained from subspecies of *Bacillus thuringiensis* including, but not necessarily limited to, B.t. *kurstaki* HD-1, B.t. *kurstaki* HD-73, B.t. *sotto*, B.t. *berliner*, B.t. *thuringiensis*, B.t. *tolworthi*, B.t. *dendrolimus*, B.t. *alesti*, B.t. *galleriae*, B.t. *aizawai* and B.t. *subtoxicus*. Dipteran-type toxins and structural genes encoding such toxins can be obtained from subspecies such as B.t. *israeliensis*. Coleopteran-type toxins and structural genes encoding such toxins can be obtained from subspecies of *Bacillus thuringiensis* including, but not necessarily limited to, B.t. *tenebrionis* and B.t. *san diego*. For clarity and brevity of explanation, the present invention will be further described using Lepidoperan-type toxins from B.t. *kurstaki* HD-1 and HD-73 and a Coleopteran-type toxin from B.t. *tenebrionis*.

The inhibitor used in the practice of the present invention is usually a trypsin or trypsin/chymotrypsin inhibitor from plants although other trypsin inhibitors may be used if determined to exhibit the enhancing effect on *B.t.* toxins. Specifically, suitable trypsin inhibitors may be isolated from animals, plants, insects or microorganisms.

A suitable trypsin inhibitor can be either the Kunitz or Bowman-Birk type and can be isolated from many plant species including, but not necessarily limited to, pea, cowpea, split pea, lentil bean, pinto bean, northern bean, lima bean, mung bean, mustard bean, soybean, red bean, caraway, cajun pea, rice, cotton, corn, wheat, sorghum, rapeseed, millet and barley.

Trypsin inhibitors can be isolated by numerous procedures. Typically, seeds of the source plant are ground to a course powder in a coffee grinder and stored at room temperature. Extraction of the trypsin inhibitors is accomplished by mixing the course powder in an appropriate proportion (usually 1/5 w/v) using 100 mM sodium phosphate, 150 mM sodium chlorine buffer at pH 7.0 and 4° C. The powder is kept in suspension by a rocking table or stirring on a magnetic stir plate. After 16-24 hours of mixing, the particulates are removed by first passing the suspension through three layers of cheesecloth and then centrifuging the filtrate at 14,000 × gravity (g) for 20 minutes. The supernatant is carefully removed and stored at −80° C. Alternately the ground powder can be pretreated with alcohol to defat the powder and then extracted with buffers ranging from pH 2.5 to 8.0 utilizing an appropriate buffering agent such as Tris-HCl, pH 8.0; sodium acetate pH 5.0; sodium phosphate pH 7.0, etc. The extraction time can vary from 1 to 24 hours or longer. Extraction times in excess of 24 hours usually require refrigeration to reduce bacterial contamination. Those skilled in the art recognize that conditions for extracting protease inhibitors from ground seed are quite flexible since the inhibitors are very stable and soluble. Other alternative extraction methods include, Gennis, el al. (1976) *J. Biol. Chem.* 251:3:734–740; Elfant, et al. (1985) *Proc. Soc. Exp. Biol. and Med.* 180:329–333; Boisen, et al. (1981) *Physiol. Plant* 52:167–176; Griffiths (1984) *J. Sci Food Agric.* 35:481–486; and Wagner, et al. (1967) *Arch. Biochem. & Biophy.* 121:672–677.

The trypsin inhibitors are purified from the crude seed extract by first concentrating the protein by a salting out procedure. Powdered ammonium sulfate (enzyme grade) is added to the chilled (4° C.) crude extract with stirring on a magnetic stir plate to a concentration of about 80% (51.6 g/100 ml). A precipitate is formed and after mixing for about 1 hour is removed by centrifugation at about 20,000 × g at 4° C. for about 30 minutes. The precipitate is dissolved in the original volume of distilled water and dialyzed against running deionized water for about 2 hours. It is again dialyzed overnight against a buffer comprising 50mM sodium acetate, 20mM calcium chloride, pH 5.0 at 4° C. (~40X original volume). In most cases the lower pH will produce a precipitate which is removed by centrifugation at 14,000 × g for 20 minutes and discarded. The supernatant which contains the fraction of inhibitor protein is stored at −80° C. for further purification.

Several methods of column chromatography can be utilized to isolate the various types of protease inhibitors from seed extracts. Due to the low molecular weight (6,000–25,000 Kd) of plant inhibitors, Foard and co-workers, *Biochem. & Biophys. Act.* (1977) 495:369–382, purified plant inhibitors by chromatographic means using Sephadex G-100, Sephadex G-75 and finally ion exchange on DEAE-cellulose. Modifications of this general protocol have been used by others to purify seed inhibitors.

In addition, recent advances in affinity chromatography techniques provide a potentially valuable tool for purification of inhibitors. The specificity of inhibitors toward trypsin and chymotrypsin may be utilized to also separate Kunitz (trypsin inhibitor) type from the Bowman-Birk (double-headed chymotrypsin/trypsin inhibitors) type of seed inhibitors.

Anhydrotrypsin-Sepharose and anhydrochymotrypsin-Sepharose are prepared by activation of Sepharose 4B-CL with cynanogen bromide (2g/ml acetonitrile) and maintaining the reaction at a temperature below 10° C. and pH greater than 10 until the pH stabilizes. The activated resin is extensively washed with ice cold distilled water and 100 mM sodium bicarbonate and mixed 1:1 with anhydrotrypsin or anhydrochymotrypsin (see *Methods in Enzymology*, Vol. 91, pp. 378–388 Academic Press, 1983). Typically the coupling is greater than 98% complete after overnight incubation at 4° C. The resin is extensively washed with distilled water and 10 mM HCl and remaining reactive sites blocked with equal volume of 2M ethanolamine pH 9.0 overnight. The resin is washed a second time and stored at 4° C. Sequential chromatography on anhydrotrypsin-Sepharose and then anhydrochymotrypsin-Sepharose is typically carried out using 50 mM sodium acetate, 20 mM calcium chloride at pH 5.0. Protein from the ammonium sulfate step is loaded onto an anhydrotrypsin-Sepharose. The column is washed with buffer and eluted with 5mM HCl. Peak fractions (A280) are pooled, buffered to pH 5.1 and applied to a anhydrochymotrypsin-Sepharose column which was washed and eluted exactly as described above for the anhydrotrypsin-Sepharose column. The flow-through fractions contain Kunitz inhibitor whereas the HCl eluted fractions contained the Bowman-Birk inhibitor.

ISOLATION OF B.t. TOXIN

A. Lepidopteran-type Toxin

Numerous methods have been used to purify Lepidopteran-type toxins from B.t. bacteria; Johnson, D. E., (1975) Incidence of Insect Cell Cytolytic Activity Among *Bacillus thuringiensis* serotypes. *FEMS Microbiology Lettres* 43:121–125; Lecadet, M. M. and Dedonder, R. (1971) Biogenesis of the Crystalline Inclusion of *B. thuringiensis* during sporulation. Eur. J. *Biochem.* 23:282–294; Schesser, J. H., Kramer, K. J. and Bulla, Jr. L. A. (1977) Bioassay for Homogeneous Parasporal Crystal of *Bacilus thuringiensis* using the Tobacco Budworm, Manduca Sexta, *Appl. Environ. Microbiol.* 33:878–880; Tojo, A. and Aizawa, K. (1983) Dissolution and Degradation of *Bacillus thuringiensis&* Endotoxin by gut juice Protease of the Silkworm Bombyx, *Appl. Environ. Microbiol.* 45:2:576–580; Nickerson, K. W. and Bulla, Jr. L. A. (1974) *Appl. Microbiol.* 28:124–128. One method to isolate the toxin from B.t.k. HD-73 bacteria is disclosed by Yamamoto et al., 1983, *Arch. of Biochem. & Biophys.* 227:1:233–241. The bacteria are grown in a culture medium containing peptonized milk nutrient, glucose, yeast extract, potassium phosphate monobasic and other trace minerals. Fermentation is maintained at 30° C. until almost all cells produce spores and crystals. The cells are lysed and the crystals are harvested by centrifugation at 10,000 g for 2 min. and washed in 1 M NaCl by repeating the centrifugation at least three times to remove bacterial proteases. The mixture of spores and crystals are suspended in water and shaken in a separatory funnel until foam develops. The crystals in the aqueous layer are separated from the spore-containing foam layer, and this separation by foaming is repeated at least 10 times until almost all spores are removed. The crystals are further purified by isopycnic centrifugation using a sodium bromide (NaBr) density gradient. An aliquot of the crystal suspension is layered on a linear density gradient of NaBr (1.30 to 1.40 g/ml) and centrifuged at 100,000 g for 2 hours. The crystal band is located by examining each band with a phase contrast microscope. The NaBr is removed from the crystals by centrifugation followed by dialysis in water. The purified crystals are lyophilized and stored at −20° C. until used.

Lyophilized crystals (100 mg) are suspended in 4 ml water and incubated at 70° C. for one hour in a mechanically convected oven to inactivate any remaining bacterial proteases. The crystals are then dissociated by addition of 2-mercaptoethanol at the final concentration of 2% and sodium hydroxide to adjust the pH to 10. The liberated toxins are purified on a Sepharcyl S-300 (Pharmacia) column equilibrated with 50 mM Tris-HCl, pH 8, containing 0.1% 2mercaptoethanol and 1 mM EDTA. The toxin is collected and concentrated by acid precipitation at a pH equal to the isoelectric point of the toxin.

For the proteolytic cleavage of HD-73, gut juice was collected from fifth-instar larvae of the cabbage looper (*T. ni.*) and linked to Sepharose 4B by the cyanogen bromide method as described on page 9. Purified B.t.k. HD-73 was mixed with T. ni. gut juice —Sepharose in a 1:1 ratio and incubated at 25° C. with gentle stirring for 4 hours. The solution was centrifuged at 6,000 × g to remove the resin and analyzed on SDS-PAGE for extent of cleavage (conversion of 134 Kd to 68 Kd protein). Once the reaction was determined to be complete, the protein was lyophilized and stored at −80° C.

B. Coleopteran-type Toxin

B.t. var. *tenebriosis* (B.t.t.) produces a number of Coleopteran-type toxin proteins, present in protein crystals, which are produced co-incidentally with sporulation. These protein crystals are released into the media as cells autolyse during or following sporulation. To determine the number of toxin proteins produced by B.t. var. *tenebrionis,* 500 ml cultures of this organism were grown in 2 liter flasks in 15% TSB medium in 100 mM 2-(N-morpholino) ethansulfonic acid (MES) buffer, pH 7.0 at 30° C. for 7 days. At this point the cultures have sporulated and the cells lysed. Protein crystals and spores were harvested by centrifugation at 20,000 x gravity (g) for 20 min. at 4° C. Pellets were washed three times with excess water, followed by three washes with 2 M NaCl. The resultant pellet was stored at 4° C. in water plus 0.02% sodium azide. B.t.t. toxin protein was solubilized from the crystals by suspending the pellet in 100 mM sodium carbonate buffer, pH 10 and stirring this suspension for two hours at room temperature. After centrifugation at 20,000 xg for 20 min. to remove unsolubilized materials, the supernatant was filtered through a 0.2 μm filter to remove any remaining spores. B.t.t. toxin protein prepared in this manner, as do crystals solubilized in 125 mM Tris-HCl, 4% SDS, 20% glycerol and 10% 2-mercaptoethanol, pH 6.8, (SDS sample buffer used to prepare samples for SDS-PAGE analysis) is comprised of four major and different proteins as judged by SDS-PAGE analysis.

PREPARATION OF B.t. TOXIN/PROTEASE INHIBITOR COMPOSITIONS

The insecticidal compositions of the present invention comprise a toxin protein(s) from a strain of *Bacillus thuringiensis* and an effective amount of a suitable trypsin inhibitor to enhance the insecticidal activity of the respective toxin protein. In most cases the amount of protease inhibitor will comprise between 0.0000002 and 2.0 wt % of the diet. However, in many cases effective insecticidal enhancement of the toxin can be obtained with inhibitor levels less than 0.02 wt %, levels which are far below the inhibitor levels which exhibit insecticidal activity alone. In many cases it will be possible to use crude preparations of B.t. toxin which comprise sporulated cultures containing the endogenous toxin protein. The inhibitor is present in a molar ratio versus toxin between $1/10^{-2}$ to $10^6/1$ when the toxin is present at a concentration between and $10^{-10}$ and $10^{-7}$ M. An inhibitor/ toxin ratio between about 1/1 and $10^4/1$ is preferred. Those skilled in the art recognize that the potentiating effect due to the presence of inhibitor will vary with the target insect.

The improved insecticidal compositions may also include a suitable carrier such as vermiculite, silica, etc. The composition may also be dispersed in a polymer to enhance its handling characteristics and enhance its tolerance to degradation due to environment conditions particularly exposure to ultraviolet light. A trypsin inhibitor gene can be engineered for expression in *Bacillus thuringiensis* in order to produce by fermentation a microbial insecticide that contains appropriate levels of both B.t. protein and trypsin inhibitor.

A cloned trypsin inhibitor gene can be introduced into by transformation using the method of Heierson et al., (1987) or by the method of Crawford, et al., (1987). These groups have shown that transformation of B.t. can be obtained with plasmids derived from *B. subtilis* that express resistance to kanamycin, tetracycline plus erythromycin, tetracycline or chloramphenicol. In addition, at least two different types of plasmid replicons have been used successfully. Based on the work of these groups, plasmids pGR71, pTV53ts, pBC16 or pC194 could be used as vectors to deliver a trypsin inhibitor gene into B.t. Other plasmids with similar selectable markers and replicons could also be used.

Appropriate trypsin inhibitor coding sequences for expression would be the cDNA for soybean Kunitz trypsin inhibitor or tee synthetic gene for carcurbeta maxima trypsin inhibitor (CMTI) from squash. To express these genes in B.t. it is necessary to fuse them at their 5' ends to a promoter capable of expressing in B.t. Suitable promoters could be derived from the 5' flanking regions of the antibiotic resistance genes known to function in the transformation vectors. Promoters known to function in *B. subtilis* are also likely to function in B.t. Several promoters of this type have been described. These promoters ar mostly known to express in vegetative cells and so would lead to the production of inhibitor before the toxin protein.

It might also be appropriate to express trypsin inhibitor coordinately with protein during crystal formation. This could be achieved by fusing the inhibitor gene to the toxin gene promoter. An appropriate fragment containing this promoter would be the approximately 150 bp segment extending from the HpaI site upstream of the B.t.k. gene in pMAP3 to the ATG at the start of the toxin gene. Trypsin inhibitor genes fused to this fragment would express toxin and inhibitor coordinately. Other sporulation specific promoters are known in (reference) and would likely work in *B. subtilis* (reference) and would likely work in B.t.

INSECT-RESISTANT PLANTS

In another embodiment of the present invention, the ability of plants to resist attack by insects can be enhanced by expressing both the B.t. toxin and a trypsin inhibitor in the transgenic plant.

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which causes the addition of polyadenylate nucleotides to the 3' end of the RNA.

Transcription of DNA into mRNA is regulated by a region of DNA usually referred to as the "promoter". The promoter region contains a sequence of bases that signals RNA polymerase to associate with the DNA, and to initiate the transcription of mRNA using one of the DNA strands as a template to make a corresponding strand of RNA.

A number of promoters which are active in plant cells have been described in the literature. These include the nopaline synthase (NOS) and octopine synthase (OCS) promoters (which are carried on tumor-inducing plasmids of *Agrobacterium tumefaciens*), the cauliflower mosaic virus (CaMV) 19S and 35S promoters, the light-inducible promoter from the small subunit of ribulose bis-phosphate carboxylase (ssRUBISCO, a very abundant plant polypeptide), and promoters of genes encoding hydroxproline-rich glycoproteins. All of these promoters have been used to create various types of DNA constructs which have been expressed in plants; see e.g., PCT publication WO 84/02913 (Rogers et al., Monsanto).

Promoters which are known or are found to cause transcription of RNA in plant cells can be used in the present invention. Such promoters may be obtained from plants or plant viruses and include, but are not limited to, the CaMV35S promoter and promoters isolated from plant genes such as ssRUBISCO nopaline synthase (NOS) and mannopine synthase (MAS) genes. As described below, it is preferred that the particular promoter selected should be capable of causing sufficient expression to result in the production of toxin protein and protease inhibitor. The amount of toxin protein and protease inhibitor needed to induce resistance may vary with the type of plant and/or insect to be protected against. Accordingly, while the CaMV35S promoter is preferred, it should be understood that this promoter may not be the optimal one for all embodiments of the present invention.

The promoters used in the DNA constructs of the present invention may be modified, if desired, to affect their control characteristics. For example, the CaMV35S promoter may be ligated to the portion of the ssRUBISCO gene that represses the expression of ssRUBISCO in the absence of light, to create a promoter. which is active in leaves but not in roots. The resulting chimeric promoter may be used as described herein. For purposes of this description, the phrase "CaMV35S" promoter thus includes variations of CaMV35S promoter, e.g. promoters derived by means of ligation with operator regions, random or controlled mutagenesis, etc.

The DNA constructs of the present invention also contain structural genes encoding a plant protease inhibitor and/or a B.t. toxin protein. Exemplary structural genes for both the plant protease inhibitor and toxin are described hereinafter. Those skilled in the art will recognize that similar techniques may be used to prepare other structural genes encoding other B.t. toxins or plant protease inhibitors.

A coding sequence used in a DNA construct of this invention may be modified, if desired, to create mutants, either by random or controlled mutagenesis, using methods known to those skilled in the art. Such mutants and variants are therefore within the scope of the present invention. Accordingly, the phase "B.t. toxin" is used here to include truncated toxins as well as fulllength B.t. toxin. The phrase "protease inhibitor" is used here to include mutant and variant inhibitors as well as unmodified protease inhibitors.

The 3' non-translated region contains a polyadenylation signal which functions in plants to cause the addition of polyadenylate nucleotides to the 3' end of the mRNA. Examples of suitable 3' regions are (1) the 3' transcribed, non-translated regions containing the polyadenlated signal of Agrobacterium the tumorinducing (Ti) plasmid genes, such as the nopaline synthase (NOS) gene, and (2) plant genes like the soybean storage protein genes and the small subunit of the RuBP carboxylase gene. An example of a preferred 3' region is that from the NOS gene, described in greater detail in the examples below.

The RNA produced by a DNA construct of the present invention also contain a 5' non-translated leader sequence. This sequence can be derived from the promoter selected to express the gene, and can be specifically modified so as to increase translation of the mRNA. The 5' non-translated regions can also be obtained from viral RNA'S, from suitable eukaryotic genes or from a synthetic gene sequence.

INSERTION OF GENES INTO PLANTS

The genes employed in the practice of the present invention can be inserted into the genome of a plant by any suitable method. Suitable plant transformation vectors include those derived from a tumor inducing plasmid of Agrobacterium such as those described by Herrera-Estralla, et al. (*Nature* 303:209, 1983), Bevan, et al. (Nature 304:184, 1983), Klee, et al. (*Bio/Technology* 3:637, 1985), Fraley, et al. (*Bio/Technology* 3:629, 1985), and Schilperoort, et al. (EPO publication 120,516). In addition to plant transformation vectors derived from tumor inducing plasmids of Agrobacterium, alternative methods can be used to insert genes into plant cells. Such methods may involve, for example, the use of liposomes, electroporation, chemicals that increase the free DNA uptake. Plant cells transformed with B.t. and trypsin inhibitor genes are regenerated into whole plants which exhibit enhanced insect resistance. Choice of methodology for the regeneration step is not critical, with suitable protocols being available for hosts from Leguminosae (alfalfa, soybean, clover, etc.), Umbelliferae (carrot, rapeseed, etc.), Cucubitaceae (melons and cucumber), (potato, tobacco, tomato, peppers) and various floral crops. See, e.g. Ammirato, et al. (1984) *Handbook of Plant Cell Culture—Crop Species* (MacMillan Publ. Co.), Plants from each of the aforesaid families can be rendered insect resistant pursuant to the present invention.

(A) Construction of Structural Trypsin Inhibitor Gene

A gene encoding a trypsin inhibitor can be isolated and constructed by numerous methods. Where the total amino acid or nucleotide sequence is already known (e.g. squash, potato inhibitors) the gene can be constructed directly by synthesizing the complete gene (see below). When the protein and DNA sequence is unknown, antibodies can be produced against the protease inhibitor and a cDNA library screened immunologically for clones which produce the protease inhibitor. As an alternative, the amino-terminal amino acid sequence of the protease inhibitor can be determined by a variety of methods and a cDNA library screened using degenerate oligonucleotide probes to detect clones which contain the protease inhibitor gene (see Kunitz inhibitor cloning below as an example).

The N-terminal amino acid sequence of a protease inhibitor is determined for an inhibitor preparation prepared as described above using known methods routine to those skilled in the art. For example, the protease inhibitor can be purified as described above and its N-terminal amino acid sequence determined directly. Alternatively, a protein preparation including the protease inhibitor can be applied to a polyacrylamide gel, the proteins separated electrophoretically and the protease inhibitor band electroluted and sequenced.

(i) Synthetic Gene for Plant Expression of CMTI

A trypsin inhibitor called CMTI has been isolated from squash and shown to potentiate the activity of B.t.k. against Lepidopteran insects and the activity of B.t.k. against Colorado potato beetle. The amino acid sequence of CMTI is:

RVCPRILMKC KKDSDCLAEC VCLEHGYCG

Based on this amino acid sequence a synthetic gene has been designed. This synthetic gene is designed to include codons that are preferentially found in highly expressed genes of dicotyledonous plants. The gene is assembled from four synthetic oligonucleotides. After annealing and ligation, the synthetic gene has the DNA sequence:

```
agat ct agcat gcgt gt t t gcccaagaat cct cat gaagt gcaagaaagacagcgat t gc
-----------+-----------+-----------+-----------+-----------+-----------+-
t ct agat cgt acgcacaaacgggt t ct t aggagt act t cacgt t ct t t ct gt cgct aacg
          M  R  V  C  P  R  I  L  M  K  C  K  K  D  S  D  C
```

```
ct t gct gaat gcgt gt gcct t gagcacggat act gcggat aat aagat ct
————+————————+————————+————————+————————+
gaacgact t acgcacacggaact cgt gcct at gacgcct at t at t ct aga
  L   A   E   C   V   C   L   E   H   G   Y   C   G   *   *
```

This gene encodes the CMTI protein and is flanked by BglII sites. For expression in plants this BglII fragment is ligated into a plant expression cassette vector such as pMON893 which contains a BglII site between the enhanced CaMV35S promoter and the soybean 7S 3' end. It is also possible to use other plant promoters in order to modulate the level of expression. These vectors are mated into Agrobacterium and used to transform plants. Plants expressing CMTI are identified by northern analysis for RNA or western or ELISA analysis for protein. Plants expressing this protein are crossed with plants expressing B.t.k. or B.t.t. protein. Progeny expressing both genes are identified and show higher levels of insecticidal activity than the parent plant expressing only B.t.

Alternatively, the CMTI gene is introduced into a plant expression vector containing a selectable marker other than kanamycin resistance, such as gentamicin resistance or hygromycin resistance. This vector is used to transform a plant previously identified as expressing B.t.k. or B.t.t. The doubly transformed plant shows a higher level of activity than the parent plant expressing only B.t.

An alternative scheme for utilizing the synthetic CMTI gene is to create a fusion protein between CMTI and B.t.k. or B.t.t. This fusion could be made so that CMTI is at the N-terminus or the C-terminus of the fusion product. In the case of B.t.k. appropriate sites for fusion would be at the C-terminus at any point beyond amino acid 607, or at the N-terminus at any point before amino acid 29 and especially before amino acid 25. Placing the inhibitor sequence upstream of amino acid 25 would maintain the B.t.k. sequence which is cleaved by insect gut proteases between amino acids 28 and 29. Maintaining this sequence would allow proper cleavage of B.t.k. in the fusion which is necessary for insect toxicity. In addition, cleavage at this site would allow release of both the activated B.t.k. and the CMTI within the insect gut. In the case of B.t.t., the fusion would place the CMTI sequence either at the end of the B.t.t. protein for a C-terminal fusion. For an N-terminal B.t.t. fusion, placing the CMTI just upstream of amino acid 48 (amino terminus of band 3) would allow cleavage in the insect gut to separate the CMTI and the B.t.t. as for B.t.k. above.

In order to create these fusions at different points, the synthetic gene needs to be slightly modified at its ends to incorporate appropriate sequences to allow fusion to B.t. genes while keeping the fusion protein reading frame intact. These manipulations are done by either resynthesizing the oligonucleotides used to construct the gene or by performing site-directed mutagenesis on a cloned copy of the synthetic gene.

(ii) Preparation of cDNA Clones

In the case where the N-terminal sequence has been determined for an inhibitor protein, degenerate synthetic DNA oligonucleotide probes are designed based on the N-terminal amino acid sequence. These probes are used to screen cDNA libraries by plaque hybridization. Typical probes are 15 to 30 nucleotides in length. Regions of the amino acid sequence comprised of those amino acids having the fewest degenerate codons are preferred in order to reduce the degeneracy of the probes. Typically plaques are screened sequentially with two or more probes derived from different regions of the protein sequence; however, screening with one probe is also feasible. Plaques which hybridize with one probe are rescreened by hybridization with a second probe. Those plaques which hybridize with two or more probes are further characterized.

For clarity and brevity the methodology will be explained with reference to the Kunitz trypsin inhibitor of soybean. An inhibitor for which the amino acid sequence is known (see FIG. 1). For the soybean Kunitz trypsin inhibitor, probes are synthesized corresponding to amino acids 62 to 66 (Tyr Arg Ile Arg Phe), amino acids 114 to 118 (Met Asp Gly Trp Phe) and amino acids 125 to 130 (Asp Asp Glu Phe Asn Asn). These are regions of relatively low degeneracy; however, other regions can also be used for probe design. Degenerate probes corresponding to these regions:

| | | | |
|---|---|---|---|
| TAYAGRATHAGRTTY<br>TyrArgIleArgPhe | 62 to 66 | 15-mer | 48-fold degenerate |
| ATGGAYGGNTGGTTY<br>MetAspGlyTrpPhe | 114 to 118 | 15-mer | 16-fold degenerate |
| GAYGAYGARTTYAAYAAY<br>AspAspGluPheAsnAsn | 125 to 130 | 18-mer | 64-fold degenerate | where
Y = C or T
R = A or G
H = A or C or T
N = A or G or C or T

A cDNA library is constructed from tissue which expresses a high level of the Kunitz inhibitor. Appropriate source tissues are immature seeds, immature embryos or mid-maturation stage cotyledons.

(1) Poly-A mRNA

Total RNA is isolated from the source tissue as described by Goldberg 1981. Total RNA is further sedimented through a CsCl cushion as described by Depicker 1982. Poly-A mRNA is selected by oligo-dT cellulose chromatography.

(2) Gel Processing of RNA

Ten μg of poly-A RNA from the source tissue is precipitated with ethanol and resuspended in 1 × MOPS buffer (20 mM morpholino propane sulfonic acid, pH 7.0, 5 mM sodium acetate and 1 mM EDTA, pH 8.0) containing 50% formamide and 2.2M formaldehyde. RNA is denatured by heating at 65° C. for 10 min. One-fifth volume of a loading buffer containing 50% glycerol, 1 mM EDTA, 0.4% bromophenol blue and 0.4% xylene cyanol is then added. RNA is fractionated on a 1.3% agarose gel containing 1.1M formaldehyde until bromophenol blue is near the bottom. HaeIII-digested φX174 DNA, labelled with $^{32}$P, is run as a size standard. The DNA markers indicated approximate sizes for the RNA bands.

(3) Transfer of RNA to Nitrocellulose

RNA is transferred to nitrocellulose (#BA85, Schleicher & Schuell, Keene, NH) by blotting the gels overnight using 20X SSC (1X SSC is 0.15M NaCl, 0.015M sodium citrate, pH 7.0) as the transfer buffer. After transfer, filters are air-dried and baked in a vacuum oven for 2-3 hours at 80° C.

(4) Preliminary Hybridization with Radioactive Probes

Filters are prehybridized in 6 x SSC, 10 × Denhardt's solution (1 × Denhardt's solution is 0.02% ficoll, 0.02% polyvinylpyrrolidone, 0.02% bovine serum albumin), 0.5% NP-40, and 200 μg/ml *E. coli* transfer RNA at 50° C. for 4 hours. Hybridization is carried out in the fresh solution containing $2 \times 10^6$ cpm/ml of the selected probe for 48 hours at 32° C. Hybridization temperature (32° C.) used in each case is about 10° C. below the dissociation temperature (Td) calculated for the oligonucleotide with the lowest GC content in a mixture. The Td of the probe is approximated by the formula $2° C. \times (A+T) + 4° C. \times (G+C)$.

(5) Filter Washing

The filters are washed twice for 15-20 minutes at room temperature in $6 \times SSC$ and then for 5 minutes at 37° C. with gentle shaking. Filters are then wrapped in plastic film and autoradiographed for 12-14 hours at $-70°$ C. with two intensifying screens. This allows the determination of the size and abundance of the protease inhibitor mRNA.

B. Preparation of λgt10 cDNA Library (1) Materials Used

AMV reverse transcriptase can be purchased from Seikagaku America, Inc., St. Petersburg, Florida; the large fragment of DNA polymerase I (Klenow polymerase) from New England Nuclear, Boston, Mass.; S1 nuclease and tRNA from Sigma Chemical, St. Louis, Mo.; AcA 34 column bed resin from LKB, Gathersburg, Md.; EcoRI, EcoRI methylase and EcoRI linkers from New England Biolabs, Beverly, Mass.; RNasin (ribonuclease inhibitor) from Promega Biotech, Madison, Wis. and radioactive compounds from Amersham, Arlington Hts., Ill..

The λgt10 vector (ATCC No. 40179) has three important characteristics: (1) it has a unique EcoRI insertion site, which avoids the need to remove a center portion of DNA from the phage DNA before inserting new DNA; (2) DNA ranging in size from zero to about 8,000 bases can be cloned using this vector; and (3) a library can be cloned using this vector; MA150 cells (ATCC No. 53104) were utilized to remove clones which do not have DNA inserts.

(2) cDNA First Strand Synthesis

Poly-A mRNA is prepared as described above and resuspended in 50 mM Tris-HCl (pH 8.5), 10 mM $MgCl^2$, 4 mM DTT, 40 mM KCl, 500 μM of d(AGCT)TP, 10μg/ml $dT^{12}$ $^{18}$primer, and 27.5 units/ml RNasin. In a 120 μl reaction volume, 70 units reverse transcriptase are added per 5 μg of poly-A RNA. One reaction tube contains α-$^{32}$P-dCTP (5 μC:/120 μl reactions). In order to disrupt mRNA secondary structure, mRNA in H₂O is incubated at 70° C. for 3 minutes and the tube was chilled on ice. Reverse transcriptase is added and the cDNA synthesis is carried out at 42° C. for 60 minutes. The reaction is terminated by the addition of EDTA to 50 mM. cDNA yield is monitored by TCA precipitations of samples removed at the start of the reaction and after 60 minutes. Following cDNA synthesis, the cDNA exists as a cDNA-RNA hybrid. The cDNA-RNA hybrid is denatured by heating the mixture in a boiling water bath for 1.5 minutes and cooled on ice.

(3) Second Strand Synthesis and Methylation

The first strand is dried to ca. 10 μl in a Savant speed vacuum.

| Volume | Substance | Final Conc./Amount |
|---|---|---|
| 3.8 μl | cDNA | ~500 ng of first strand |
| 10 μl | 10X Sec. Strand Buffer | 1 X |
| 0.8 μl | 5 mM dNTP | 40 μM each |
| 81.5 μl | Water | to 100 μl final volume |
| 2 μl | DNA Pol I (NEB) | 20 U |
| 0.4 μl | *E. coli* DNA ligase (NEB) | 2 U |
| 0.5 μl | RNAase H (BRL) | 1 U |
| 3 μl | 32P dCTP | 30 μCi |
| 1 μl | BSA (1:10 dil of BRL) | 50 μg/ml) |

NEB = New England Biolabs, Beverly, MA.
BRL = Bethesda Research Labs, Gaithersberg, MD.

The reaction is incubated at 14° C. for 60 min. then at room temperature for 60 min.

The following are added:

| 0.5 μl | 5 MM dNTP |
| 1 μl | T4 DNA polymerase (NEB) |

The reaction is incubated for 30 min. at room temperature.

The following are added:

| 1.2 μl | 1 mM S-adenosyl L-methiononine (Sigma) | 12 μM |
| 1.0 μl | EcoRI Methylase (NEB) | 20 U |
| 2.4 μl | 0.5 M EDTA | 12 mM |

5 μl is removed from the reaction and added to 260 ng wild type lambda DNA (NEB) as control for methylation.

The reactions are incubated at 37° C. for 45 min

Both the main and test reactions are heated at 68° C. for 10 min. to inactivate enzymes.

| 10X Second Strand Buffer: | | |
|---|---|---|
| 200 mM | Tris-HCl pH 7.4–7.5 | 1 M stock |
| 50 mM | MgCl₂ | 1 M stock |
| 1.0 M | KCl | 4 M stock |
| 100 mM | Ammonium sulfate | 1 M stock |
| 1.5 mM | Beta-NAD | 150 mM stock |

C, Assay for Completeness of Methylation

The following is added to the heat treated test methylation:

| 2 μl | 100 mM Tris-HCl pH 7.6/100 mM MgCl₂/1.0 NaCl |
| 12 μl | water |
| 1 μl | EcoRI (20 units BRL) |
| 0.5 μl | pUC19 (0.5 μg, NEB) |

The reaction is incubated for 1 hour at 37° C. The products were run on an agarose minigel with undigested pUC19, and lambda digested with EcoRI and HindIII as size markers. The pUC19 in the reaction should digest to completion indicating that the EcoRI was working efficiently, the lambda DNA should remain completely undigested showing that it had been protected by the methylation reaction. This demonstrates that the methylase was effective in blocking the EcoRI sites in the cDNA from digestion.

(5) Addition of EcoRI linkers to cDNA

To insert the ds cDNAs into the EcoRI site of λgt10, blunt-ended EcoRI linkers are added to the ds cDNAs following methylation. The ds cDNAs are mixed with phosphorylated, blunt-ended EcoRI linker. The linker is a self annealed mixture of the synthetic 8-mer p(dGGAATTCC). Typically, at least a 10-fold molar excess of linker to ds cDNA is used. The linker and cDNA are ligated in a 20 μl reaction containing 10 mM Tris-HCl pH 7.5, 10 mM MgCl$_2$, 1 mM ATP, 10 mM DTT and sufficient T4 DNA ligase to ensure at least 90% completion. The reaction is incubated at 14° C. overnight. After the addition of the linkers, the linkers are cleaved with EcoRI to allow ligation into EcoRI cleaved λgt10.

(6) Assembly of λgt10 Clones

The ds cDNA is mixed with 1 μg of EcoRI-cut λgt10 DNA, precipitated with ethanol and centrifuged. After washing the pellet once with 70% ethanol, the DNA pellet is air dried and resuspended in 4.5 μl of 10 mM Tris-HCl pH 7.5, 10 mM MgCl$_2$, 50 mM NaCl. To anneal and ligate the cDNA inserts to the left and right arms of the λgt10 DNA, the mixture is heated at 70° C. for 3 minutes, then at 50° C. for 15 minutes. The mixture is chilled on ice, and 0.5 μl each of 10 mM ATP, 0.1 M DTT, and sufficient T4 DNA ligase to ensure at least 90% completion is added. The reaction is incubated at 14° C. overnight, which allowed the insertion of the ds cDNA into the EcoRI site of the λgt10 DNA. The resulting DNA is packaged into phage particles in vitro using the method described by Scherer 1981.

(7) Removal of Phages without Inserts

Insertion of a cDNA into the EcoRI site of λgt10 results in inactivation of the Cl gene. λgt10 phages with inactivated Cl genes (i.e. with inserts) replicate normally in *E. coli* MA150 cells. By contrast, λgt10 phages without inserts are unable to replicate in the MA150 strain of *E. coli*. This provides a method of removing λgt10 clones which do not have inserts.

The phages in the library are first replicated in *E. coli* C600 (M+R−) cells which modified the λgt10 DNA to protect it from the *E. coli* MA150 restriction system. A number of *E. coli* C600 cells are infected and then plated with a 20 fold excess of MA150 (M+R+) cells. The primary infection thus occurred in the M+R−cells where all the phages will grow, but successive rounds of replication occurred in the MA150 cells which prevented the replication of phages without inserts. The amplified phage library is collected from the plates and after removal of agar and other contaminants by centrifugation, the recombinant phages are ready to use in screening experiments.

(8) Screening of cDNA Library

Approximately 6000 phages (each plate) are spread on 10 cm × 10 cm square plates of solid NZY agar (with 0.7% agarose) containing a translucent lawn of *E. coli* MA150 cells growing thereon (Maniatis, 1982). Areas where the phages infect and kill the *E. coli* cells are indicated by clear areas called "plaques", which are visible against the lawn of bacteria after an overnight incubation of the plates at 37° C. Several plates are prepared in this manner. The plaques are pressed against pre-cut nitrocellulose filters for about 30 minutes. This forms a symmetrical replica of the plaques. To affix the phage DNA, the filters are treated with 0.5 M NaOH and 2.5 M NaCl for 5 minutes. The filters are then treated sequentially with 1.0 M Tris-HCl, pH 7.5 and 0.5 M Tris-HCl, pH 7.5 containing 2.5 M NaCl to neutralize the NaOH. They are then soaked in chloroform to remove bacterial debris. They are then air dried and baked under a vacuum at 80° C. for 2 hours, and allowed to cool to room temperature. The filters were then hybridized with $^{32}$P-labelled inhibitor probe ($2\times 10^6$ cpm/filter) as described previously. After 48 hours of hybridization, the filters are washed in 6×SSC. at room temperature twice for 20 minutes and then at 37° C. for 5 minutes. These washes removed non-specifically bound probe molecules, while probe molecules with the exact corresponding sequence bound to the phage DNA on the filter. The filters are analyzed by autoradiography after the final wash. Plaques giving a positive hybridization signal as determined by autoradiography are removed from the plates and replated on the fresh plates at a density of 100–200 plaques/plate. These plates are screened using the procedure described above. The positively hybridizing phages are selected. DNA was isolated from each of these clones and digested with EcoRI to determine the sizes of the cDNA inserts.

Phages having cDNA inserts whose size is that expected for a full-length cDNA based on the size of the mRNA determined above are further analyzed. The EcoRI fragments corresponding to the cDNA inserts are purified by agarose gel electrophoresis, and the DNA is recovered from the gel. The cDNA inserts are inserted into the EcoRI site of filamentous phage vector such as M13 mp18. The ends of the inserted cDNAs are subjected to DNA sequence analysis. The sequence of both ends of the insert are determined. The DNA sequence is compared to the known N-terminal amino acid sequence of the protease inhibitor in order to locate the translation initiator codon. Enough DNA sequence is determined to also locate the end of the protease inhibitor coding sequence.

(9) Construction of plant vectors for the expression of protease inhibitors.

The cDNA for the protease inhibitor is engineered to position restriction sites just flanking the coding sequence. Typically, BglII sites are used. The sites are introduced into the cDNA by oligonucleotide-directed mutagenesis as described below. The engineered coding sequence is isolated as a BglII fragment and inserted into the BglII site of expression cassette vectors, such as pMON316 (see FIG. 2) to put the cDNA under the control of a plant promoter such as CaMV35S. Using a variety of promoters such as NOS, MAS, or CaMV35S provides a means for obtaining varying levels of protease inhibitor in transformed plants.

C. Construction of A Structural B.t. Toxin Gene (1) Coleopteran-type B.t. Toxins B.t. *tenebrionis* was grown in Trypsticase Soybroth (TSB) medium for the isolation of protein crystals. While Lepidopteran-type crystals are routinely isolated on gradients formed from Renografin, Hypaque or NaBr, B.t.t. crystals dissolve in these gradients media. B.t.t. crystals were stable in gradients of sucrose, and sucrose gradients were used for the isolation of B.t.t. crystals.

Purified crystals are analyzed for their protein composition by SDS polyacrylamide gel electrophoresis.

Results of these experiments indicated that B.t.t. crystals contained at least two protein components with molecular weights of approximately 68 to 70 kilodaltons (kDa) and approximately 60 kDa, respectively. The relative amounts of the components are variable from preparation to preparation. In addition, it was suggested that the higher molecular weight component might consist of more than a single protein. Bernhard (1986) reported proteins of about 68 kDa and 50 kDa as components of B.t.t. crystals. Herrnstadt et al. (1986) reported that the crystals of B.t. *san diego* were composed of a protein of about 64 kDa. In contrast, Lepidopteran-type B.t. strains such as B.t. *kursaki* typically contain a higher molecular weight protein of 130 kDA to 140 kDA. This result indicates a significant difference in the structure of the Lepidopteran and Coleopteran toxin proteins.

Several approaches were taken to purifying the individual protein components of the crystal. Isoelectric focusing was not successful because all of the protein precipitated. Anion exchange high pressure liquid chromatograph (HPLC) on a Mono Q column failed to resolve the components. Cation exchange HPLC. on a Mono S column in the presence of 4 M urea resolved five peaks. Analysis of the peaks by SDS gel electrophoresis indicated that peak A contained only the higher molecular weight band from whole crystals. Peak B was rich in this higher band with small amounts of the lower band. Peak C. was rich in the lower band with significant amounts of the upper band. Peaks D and E were mixtures of both bands. In most preparations the higher molecular weight band, corresponding to peaks A and B, was the predominant protein in the crystals. For the HPLC separated material, peaks A and B represented most of the recovered protein.

The N-terminal amino acid sequences corresponding to peaks A and B were determined. Peaks A and B were found to have the same N-terminal sequence. The sequences determined were:

PEAK A AND B:

```
1               5                   10                  15
Met Asn Pro Asn Asn Arg Ser Glu His Asp Thr Ile Lys Thr Thr
```

Using this N-terminal protein sequence information, synthetic DNA probes were designed which were used in the isolation of clones containing the B.t.t. toxin gene. Probes were end-labeled with [$\gamma$-$^{32}$P] ATP according to Maniatis (1982), supra. *B. thuringiensis* var. *tenebrionis* was grown for 6 hours at 37° C. in Spizizen medium (Spizizen, J., 1958, P.N.A.S. USA 44:1072–1078) supplemented with 0.1% yeast extract and 0.1% glucose (SPY) for isolation of total DNA. Total DNA was isolated from B.t.t. by the method of Kronstad (1983), supra. Cells were grown on Luria agar plates for isolation for B.t.t. crystals used in toxicity studies.

*E. coli* cultures were routinely grown in Luria Broth (LB) with ampicillin (Ap, 200 μg/ml), kanamycin (Km, 50 μg/ml), or gentamicin (Gm, 15 μg/ml) added for plasmid selection and maintenance.

Isolation and Manipulation of DNA

Plasmid DNA was extracted from *E. coli* cells by the method of Birnboim and Doly (1979) *Nucleic Acid Res.* 7:1513–1524, and large quantities were purified using NACS-52 resin (Bethesda Research Laboratories) according to manufacturer's instructions. Restriction endonucleases, calf alkaline phosphatase and T4 DNA ligase were used according to manufacturer's instructions (New England Biolabs). Restriction digestion products were analyzed on 0.8% agarose gels electrophoresed in Tris-acetate buffer. DNA fragments for cloning were purified from agarose using the freeze-thaw method. Construction of recombinant DNA molecules was according to Maniatis (1982), supra. Transformation into *E. coli* were performed according to Maniatis (1982), supra.

Southern analysis (*J. Mol. Biol.,* 1975, 98: 503–507) was performed using the modified dried gel procedure (Conner et al., 1983). Colony filter hybridization, for detection of B.t.t. toxin clones, used the tetramethylammonium chloride method (Wood et al., 1985, *P.N.A.S.* USA 82:1585–1588).

Southern analysis of BamHI and HindIII digested B.t.t. total DNA identified a 5.8 kb BamHI and a 3.0 kb HindIII fragment which hybridized to the synthetic Al probe. BamHI fragments of DNA (5.4–6.5 kb) were purified from agarose gels and ligated to alkaline phosphatase treated BamHI digested pUC119. pUC119 is prepared by isolating the 476 bp HgiAI/DraI fragment of bacteriophage M13 and making the ends of the fragment blunt with T4 DNA polymerase (New England Biolabs). This fragment is then inserted into pUC19 that has been digested with NdeI and filled with Klenow DNA polymerase (New England Biolabs). The ligated B.t.t. and pUC119 DNA was then used to transform form *E. coli* JM101 cells. After several attempts only 150 Ap resistant colonies were obtained. HindIII fragment of B.t.t. DNA (2.8–3.5 kb) were also cloned into the HindIII site of pUC119, and 1100 colonies were obtained. All colonies were screened by colony hybridization to the Al probe based on amino acids 1–6.

A1 Probe

```
ATGAATCCTAATAATCG
     C  C  C  C
        A
        G
```

Eleven HindIII clones showed strong hybridization, but none of the BamHI colonies showed any hybridization. The colonies identified by hybridization to Al were then screened using synthetic probe A2 based on amino acids 8–13.

A2 Probe

```
GAACATGATACAATTAA
  G  C  C  G  C
              A
```

Two colonies showed hybridization to the second probe. Restriction digest patterns of the two colonies indicated that the same 3.0 kb HindIII fragment was contained in both but in opposite orientations. These clones were designated pMON5420 and pMON5421. To confirm that the clones did contain the gene from the B.t.t. toxin protein, the single stranded DNA from both clones was sequenced using degenerate probes A1 and A2 as primers for di-deoxy sequencing (Sanger, et al., 1977, *P.N.A.S.* USA 74: 5463–5467). Sequence analysis with Al probe as primer revealed an open reading frame (ORF) whose sequence was identical to amino acids 9 through 15 of the amino acid sequence determined for purified peaks A and B of the B.t.t. toxin protein. Probe A2 produced DNA sequence which began beyond the end of the determined amino sequence, but this DNA sequence was identical to sequence produced with A1. These results confirm that the desired B.t.t. toxin gene was cloned.

gene containing no 3' flanking sequence, a BglII site was introduced just after the termination codon by the method of Kunkel (P.N.A.S. USA, 1985, 82,488-492). The sequence of toxin gene around the termination codon is:

```
GTTATATAGACAAAATTGAATTTATTCCAGTGAATTAAATTAACTAGAAAGTAAAGAAG
Val Tyr Ile Asp Lys Ile  Glu Phe Ile Pro Val Asn End
```

Figure 7:
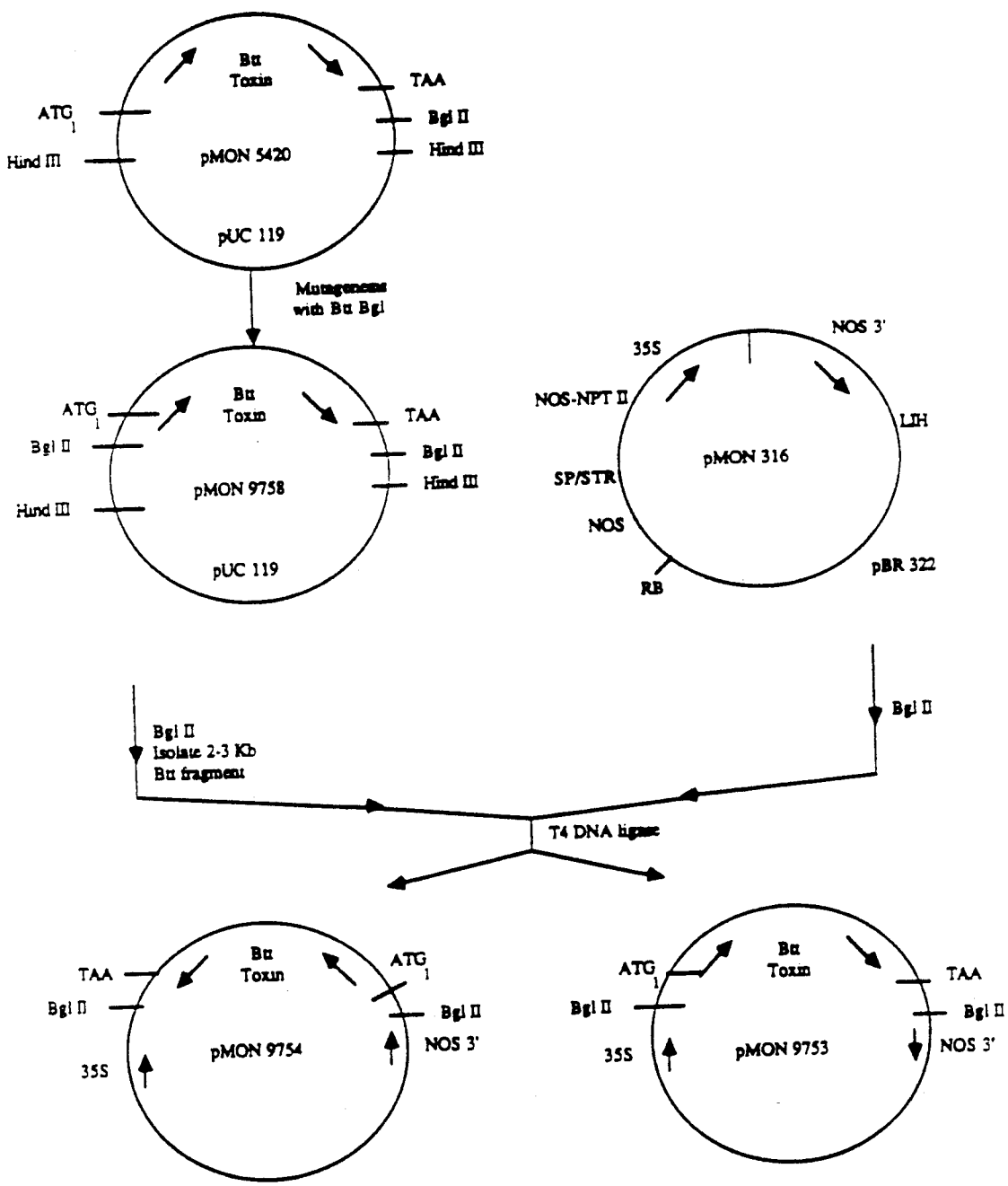
FIG. 7 shows the steps involved in the preparation of a plant transformation vector containing a gene encoding the toxin protein of B.t. *tenebrionis*.

The B.t.t. toxin gene contained in pMON5420 was modified for incorporation into plant expression vectors. Referring to FIG. 7, a BglII site was introduced just upstream of the ATG codon which specifies the initiation of translation of the full-length B.t.t. toxin protein (referred to as band 1) using the site specific mutagenesis protocol of Kunkel (P.N.A.S. USA 82:488-492, 1985). The sequence of the toxin gene in the region of the initiator ATG is:

Mutagenesis was performed with a primer (bttcterm) of sequence:

CTTTCTAGTT AAAGATCTTT AATTCACTG

Figure 12:
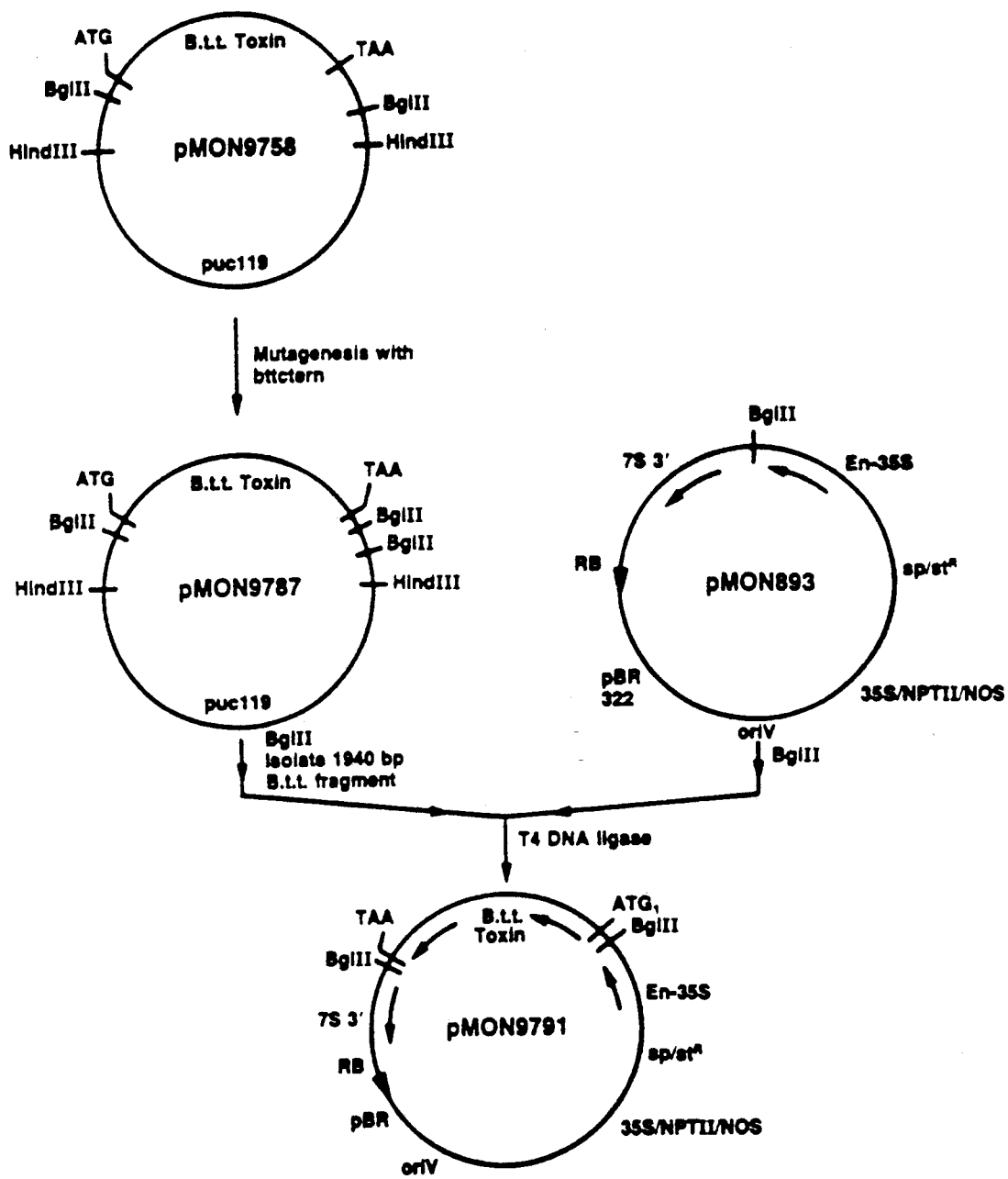
FIG. 12 shows the steps employed in the preparation of plasmid pMON9791.

Mutagenesis of the B.t.t. toxin gene was performed in pMON9758. A plasmid which contains the new BglII site was designated pMON9787 (FIG. 12). Because pMON9787 contains a BglII site just upstream of the

```
ATGATAAGAAAGGGAGGAAGAAAAATGAATCCGAACAATCGAAGTGAACATGATACAATA
                              Met Asn Pro Asn Asn Arg Ser Glu His Asp Thr Ile
```

The primer for this mutagenesis (bttbgl) was 27 nucleotides in length and has the sequence:

CGGATTCATTTTAGATCTTCCTCCCTT

Following mutagenesis a plasmid containing the new BglII site was identified by digestion with BglII and the change was verified by DNA sequence analysis. The resulting plasmid containing the B.t.t. toxin gene with the new BglII site was designated pMON9758.

The B.t.t. toxin gene in pMON9758 was inserted into the expression cassette vector pMON316 (Sanders, et al., 1987, Nucleic Acids Research 15: 1543-1558). pMON316 contains the CaMV35S promoter and the 3' end from the nopaline synthase (NOS) gene with a BglII site for gene insertion between these two elements. Plasmid pMON9758 was digested with BglII and a fragment of approximately 2.3 kb was isolated. This fragment extends from the BglII site just upstream of the ATG codon to a BglII site found approximately 350 bp downstream of the termination codon for the B.t.t. toxin gene. Thus, this fragment contains the complete coding sequence of the B.t.t. gene and also about 350 bp of noncoding sequence 3' to the termination codon. This BglII fragment was ligated with BglII digested pMON316. Following transformation into E. coli, a colony was identified in which the B.t.t. toxin gene was inserted into pMON316 such that the 5' end of the toxin gene was adjacent to the CaMV35S promoter. This plasmid was designated pMON9753. A plasmid containing the B.t.t. toxin gene in the opposite orientation in pMON316 was isolated and designated pMON9754.

Both pMON9753 and pMON9754 are introduced by a triparental mating procedure into the Agrobacterium tumefaciens strain ASE which contains a disarmed Ti plasmid. Cointegrates between pMON9753 or pMON9754 and the disarmed Ti plasmid are identified as described by Fraley, et al. (Bio/Technology, 1985, 3:629-635), and their structures confirmed by Southern analysis of total Agrobacterium DNA.

pMON9753 contained approximately 400 bp of 3' non-coding sequence beyond the termination codon. Since this region is not necessary for toxin production it was removed from the B.t.t. toxin gene segments inserted in pMON893. In order to create a B.t.t. toxin ATG initiation codon, the full coding sequence for the B.t.t. toxin gene with essentially no 5' or 3' flanking sequence is contained on a BglII fragment of about 1940 bp.

This 1940 bp fragment was isolated from pMON9787 and ligated with BglII digested pMON893. A plasmid in which the 5' end of the B.t.t. toxin gene was adjacent to the enhanced CaMV35S promoter was identified and designated pMON9791 (FIG. 12).

Figure 13:
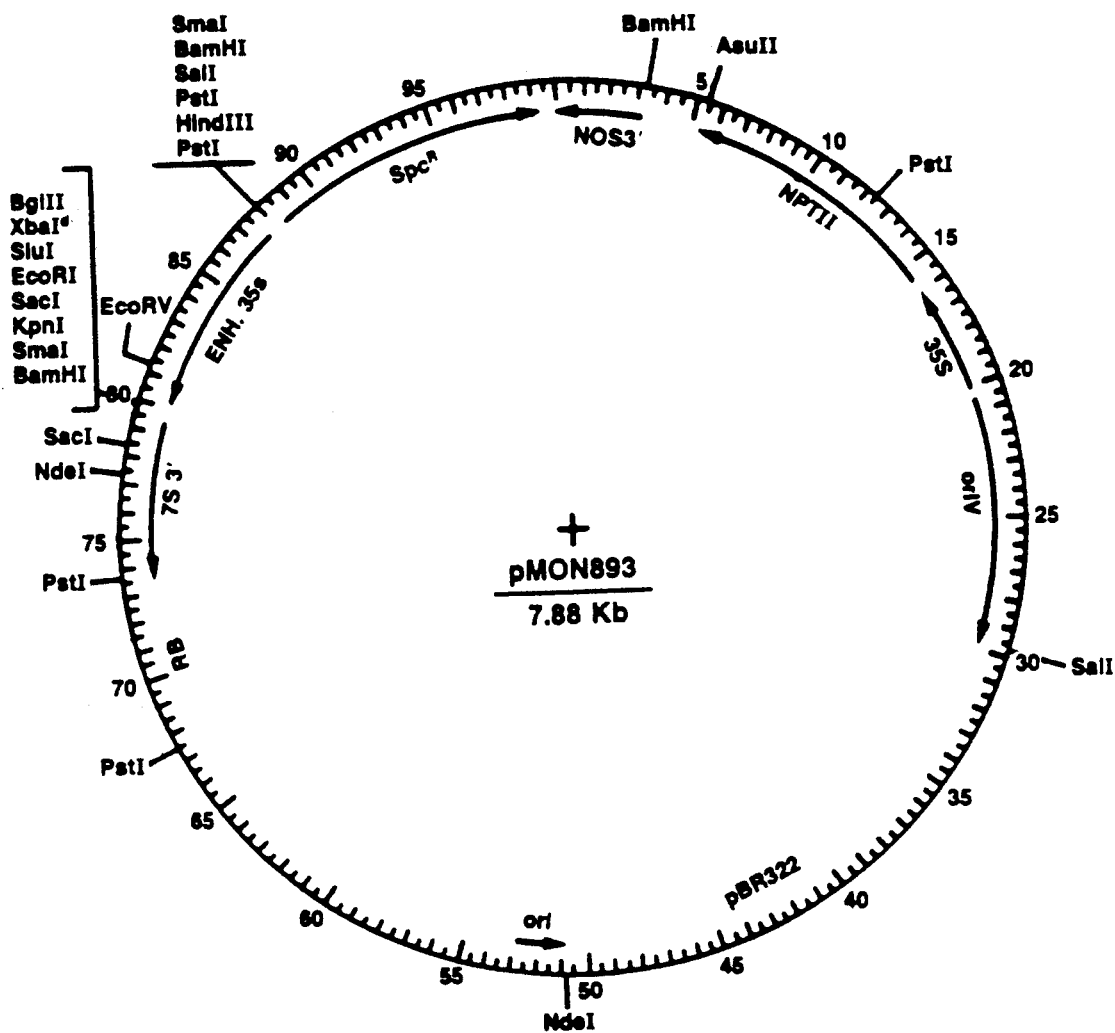
FIG. 13 shows a plasmid map for plant transformation cassette vector pMON893.

Referring to FIG. 13, the expression cassette pMON893 consists of the enhanced CaMV35S promoter and the 3' end including polyadenylation signals from a soybean gene encoding the alpha-prime subunit of beta-conglycinin (referred to below as the "7S gene"). Between these two elements is a multi-linker containing multiple restriction sites for the insertion of genes.

The enhanced CaMV35S promoter was constructed as follows. A fragment of the CaMV35S promoter extending between position −343 and +9 was previously constructed in pUC13 by Odell et al. Nature (1985) 313:810-812. This segment contains a region identified by Odell et al. as being necessary for maximal expression of the CaMV35S promoter. It was excised as a ClaI-HindIII fragment, made blunt ended with DNA polymerase I (Klenow fragment) and inserted into the HincII site of pUC18. The upstream region of the 35S promoter was excised from this plasmid as a HindIII-EcoRV fragment (extending from −343 to −90) and inserted into the same plasmid between the HindIII and PstI sites. The enhanced CaMV35S promoter thus contains a duplication of sequences between −343 and −90 (see FIG. 14).

The 3' end of the 7S gene is derived from the 7S gene contained on the clone designated 17.1 (Schuler, et al., 1982, Nucleic Acids Research 10:8225-8244). This 3' end fragment, which includes the polyadenylation signals, extends from an AvaII site located about 30 bp upstream of the termination codon for the beta-conglycinin gene in clone 17.1 to an EcoRI site located about 450 bp downstream of this termination codon.

The remainder of pMON893 contains a segment of pBR322 which provides an origin of replication in E. coli and a region for homologous recombination with the disarmed T-DNA in Agrobacterium strain ACO (described below); the oriV region from the broad host range plasmid RK2; the streptomycin resistance/ spectinomycin resistance gene from Tn7; and a chimeric NPTII gene containing the CaMV35S promoter and the nopaline synthase (NOS) 3' end, which provides kanamycin resistance in transformed plant cells.

A variant of the full length B.t.t. toxin is produced in E. coli from a second methionine initiator codon. This protein, designated "band 3", has been found to be as toxic to Colorado potato beetle as the full length toxin ("band 1"). It is possible that, as was the case for the B.t.t. gene, truncated forms of the gene might be more easily expressed in plant cells. Therefore, a modified B.t.t. toxin gene was constructed in which the region upstream of the band 3 ATG codon has been removed. In order to remove this sequence, a BglII site was inserted just upstream of the band 3 ATG by the method of Kunkel (1985). The sequence surrounding the band 3 ATG is:

CCAAATCCAACACTAGAAGATTTAAATTATAAAGAGTTTTTAAGAATGACTGCAGATAAT
Pro Asn Pro Thr Leu Glu Asp Leu Asn Tyr Lys Glu Phe Leu Arg Met Thr Ala Asp Asn

Mutagenesis was performed with primer (bttnterm) of sequence:

ATCTGCAGTC ATTGTAGATC TCTCTTTATA ATTT

Figure 15:
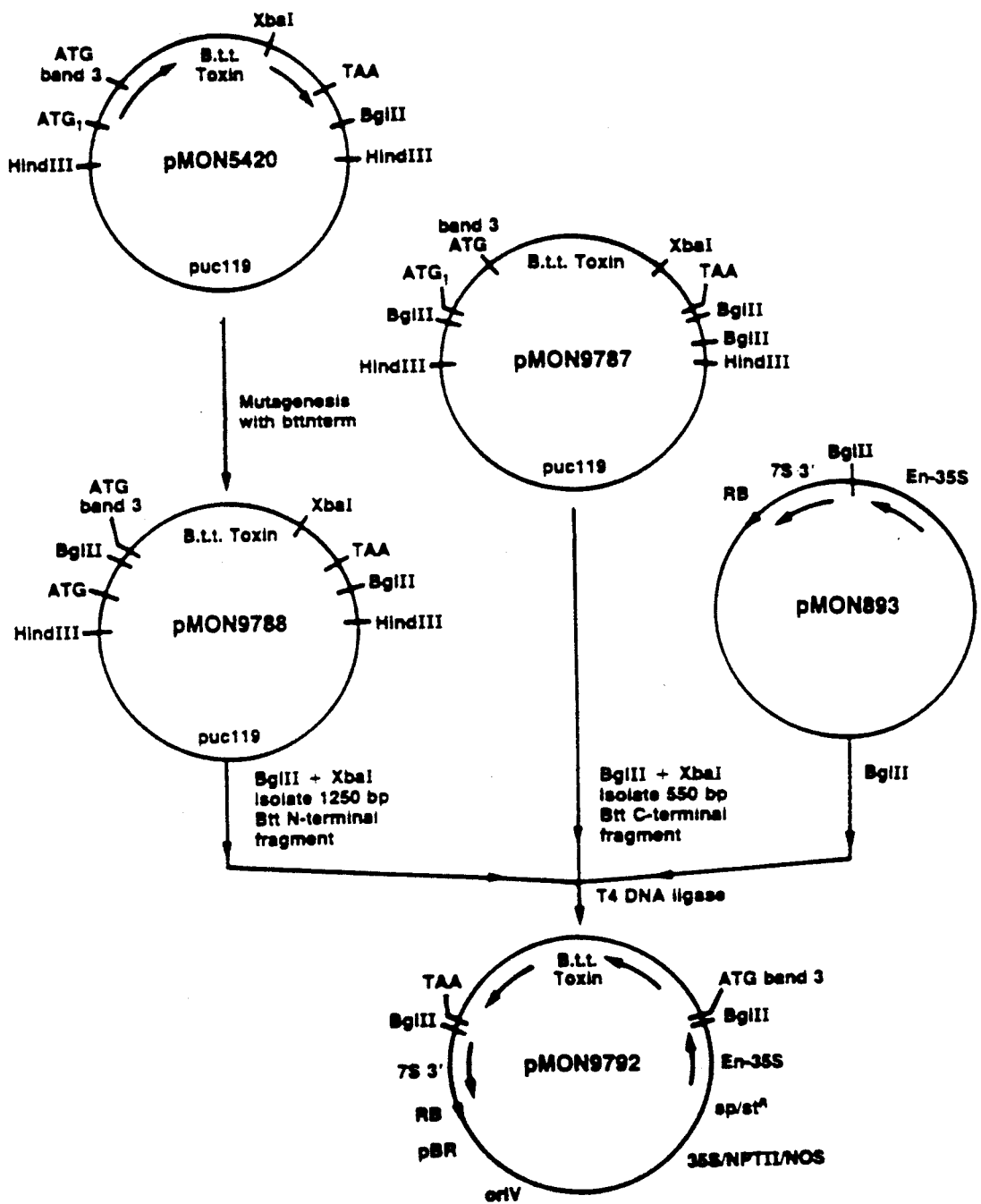
FIG. 15 shows the steps employed in the preparation of plasmid pMON9792.

Mutagenesis with this primer was performed on the toxin gene contained in pMON5420. A plasmid containing the new BglII site was designated pMON9788. A truncated B.t.t. toxin gene beginning at this band 3 BglII site and extending to the BglII site just distal to the termination codon found in pMON9787 was constructed in pMON893 as follows. pMON9788 (FIG. 15) was digested with BglII and XbaI and a fragment of about 1250 bp was isolated. This fragment extends from the band 3 ATG to a unique XbaI site in the middle of the B.t.t. toxin gene. pMON9787 was also digested with BglII and XbaI, and a fragment of about 550 bp was isolated. This fragment extends from the unique XbaI site in the middle of the toxin gene to the BglII site just distal to the termination codon. These two fragments were mixed and ligated with BglII digested pMON893. A plasmid was identified in which the 5' end to the toxin gene was adjacent to the enhanced CaMV35S promoter and designated pMON9792. pMON9792 contains a N-terminal truncated derivative of the B.t.t. toxin gene (FIG. 15) which encodes only band 3.

Both pMON9791 and pMON9792 were introduced into A. tumefaciens strain ACO which contains a disarmed Ti plasmid. Cointegrates have been selected and have been used in the transformation of tomato and potato.

Figure 16:
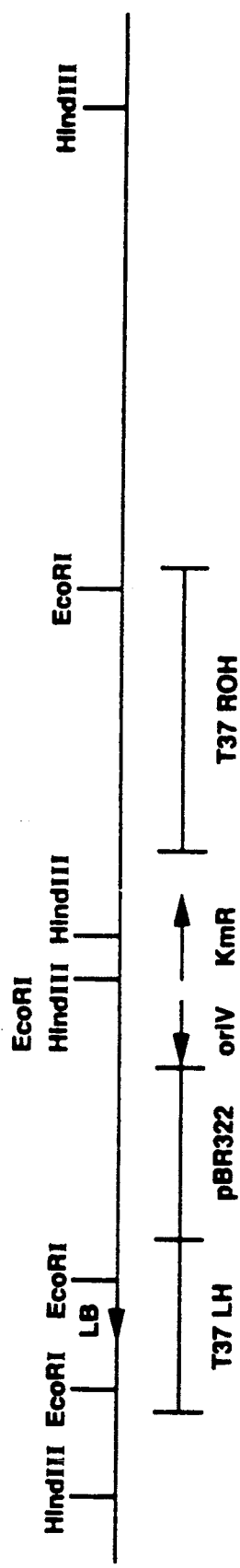
FIG. 16 illustrates the elements comprising the T-DNA region of disarmed ACO.

ACO is a disarmed strain similar to pTiB6SE described by Fraley et al. Bio/Technology (1985) 3:625-635. For construction of ACO the starting Agrobacterium strain was the strain A208 which contains a nopaline-type Ti plasmid. The Ti plasmid was disarmed in a manner similar to that described by Fraley et al. so that essentially all of the native T-DNA was removed except for the left border and a few hundred base pairs of T-DNA inside the left border. The remainder of the T-DNA extending to a point just beyond the right border was replaced with a novel piece of DNA including (from left to right) a segment of pBR322, the oriV region from plasmid RK2, and the kanamycin resistance gene from Tn601. The pBR322 and oriV segments are similar to the segments in pMON893 and provide a region of homology for cointegrate formation. The structure of the ACO Ti plasmid is shown in FIG. 16.

(2) Lepidopteran-type B.t. toxins

Isolation of DNA sequences encoding the toxin protein of B. thuringiensis is well known in the art. The coding sequence from the above-identified subspecies are quite homologous, particularly in the N-terminus region of the coding sequence. This homology is useful in the isolation of other toxin protein coding sequences, since a DNA probe useful in the isolation of B.t. subspecies kurstaki HD-1 as described hereinafter would be useful in the isolation of toxin coding sequences from other subspecies.

(i) B.t. kurstaki HD-1

The amino acid sequence of the crystal protein toxin gene isolated from Bacillus thuringiensis subspecies kurstaki HD-1 was partially determined according to the method of Hunkapiller et al. (1983) Methods Enzymol. 91:399-413. These sequences were verified using the DNA sequence of the $NH_2$-terminal portion of the crystal protein gene disclosed by Wong et al. (1983) J. Biol. Chem. 258:1960-1967. Synthetic oligonucleotide sequences based on an amino acid sequence determined from the crystal protein polypeptide were prepared according to the procedure of Beaucage et al. (1981) Tetrahedron Lett. 22:1859, see also Adams, S. P. et al. (1983) JACS, 105:661-663. The oligonucleotide probes prepared are as shown in Table I below.

TABLE I

| SYNTHETIC OLIGONUCLEOTIDE PROBES | | |
|---|---|---|
| Size | Probe Sequence | Area of B.t. Protein |
| 14-mer | TGG GGA CCG GAT TC | 1200 bp region |
| 14-mer | GAA AGA ATA GAA AC | *27-31 amino acid region |
| 21-mer | CCT GAA GTA GAA-GTA TTA GGT | *19-25 amino acid region |

*numbered from $NH_2$-terminal end

Plasmid DNA from B. thuringiensis subspecies kurstaki HD-1 was purified from 1 to 2 liters of culture according to the procedure of Kronstad et al. (1983) J. Bacteriol 154:419-428. All plasmid preparations were banded at least once in CsCl/ethidium bromide gradients. Plasmids 30 megadaltons and larger in size were preferentially isolated.

Digestion with restriction enzymes EcoRI, PstI, HindIII, BamHI and SmaI, was carried out according to conditions recommended by the supplier (Boehringer Mannheim). Escherichia coli strain JM 101 (Messing et al. 1981, Nuleic Acids Research 9:309-321) and strain SR-200 were used as the recipients for the transformation step. Competent cells were prepared according to standard procedures (Dagert et al. 1979, Gene 6:23). Colonies transformed with plasmid pUC8 were plated on L-agar with 100 μg/ml of ampicillin and 40 μl of 4% 5-bromo-4-chloro-3-indolyl-β-D-galactopyranoside (x-gal).

Plasmid DNA was transferred to nitrocellulose according to the procedure of Southern (1975) J. Molec. Biol. 98:503-517. Prehybridization was done by incubating the nitrocellulose paper with the bound transferred DNA in prehybridization fluid, 10×Denhardt's (0.2% BSA, 0.2% Ficoll, 0.2% polyvinylpyrrolidone) and 6

×SSC. (0.9M NaCl, 0.09M sodium citrate) for 2-4 hours at 37° C. Hybridization was done by incubating the nitrocellulose paper for 8-10 hours with 10-11 ml of the prehybridization fluid and the labelled probe. After several washes with 6×SSC. at increasing temperatures (30°-45° C.) the paper was exposed to X-ray film.

BamHI-restricted pBR328 (100ng), treated with alkaline phosphatase (Boehringer Mannheim) was mixed and ligated with 500 ng of *B. thuringiensis* plasmid DNA restricted with BamHI. CaCl$_2$ prepared competent *E. coli* SR200 were transformed and selected by ampicillin resistance and screened for tetracycline sensitivity. Analysis by mini-plasmid prep procedures (Maniatis et al. 1982, *Molecular Cloning, A Laboratory Manual*, Cold Spring Harbor, N.Y., p. 396) identified two clones which had the correct 16 Kb insert. Southern hybridization analysis with radiolabelled probes from Table I demonstrated that the DNA fragment which contained the sequence hybridizing to the synthetic probe had been sub-cloned. The two plasmids designated pMAP1 and pMAP2, differed only in the orientation of the DNA fragment within the vector. These plasmid constructs produced material cross-reactive to B.t. crystal protein toxin antibody when analyzed according to Western blot procedures (Geshoni et al. 1983, *Anal. Biochem.* 131:1-15 ). A restriction map of the inserted B.t. fragment was prepared and four EcoRI (E) sites and three Hind III (H) sites were located between the BamHI (B) sites. This is schematically illustrated as:

```
B    E   E E E                    B
         H H   H
```

*E. coli* strain SR200 containing pMAP2 has been deposited with the American Type Culture Collection, 12301 Parklawn Drive, Rockville, MD 20852 USA (hereinafter "ATCC") and has been designated ATCC accession number 39800.

An 8.1 Kb BamHI-PstI fragment was isolated after BamHI-PstI digestion of pMAP2 by electroelution from a preparative agarose gel onto DEAE paper used according to the directions of the manufacturer, Schleicher & Schuell, Keene, NH 03431. Plasmid pUC8 was used to sub-clone the BamHI-PstI fragment of pMAP2 carrying the gene. Ligation of pUC8 digested with BamHI and PstI with the purified 8.1 Kb BamHI-PstI fragment was followed by transformation of competent *E. coli* JM101. Transformants were selected on the basis of ampicillin resistance and a lack of β-galactosidase activity. A clone was isolated and was confirmed to contain the desired plasmid. This construct was designated pMAP3. *E. coli* strain JM101 containing pMAP3 has been deposited with ATCC and has been designated ATCC. accession number 39801.

Reduction of the *B. thuringiensis* DNA insert of pMAP3 from 8.1 Kb to 4.6 Kb was accomplished by deleting a SmaI-HpaI fragment. Plasmid pMAP3 DNA, purified by CsCl gradient centrifugation was digested with SmaI and HpaI restriction enzymes and religated. The resulting DNA fragment was utilized to transform competent *E. coli* JM101 cells. Ampicillin resistant transformants were screened by agarose electrophoresis of mini-plasmid preparations. A clone was identified which contained a plasmid with the expected DNA restriction enzyme digestion pattern. This construct was designated pMAP4.

To make a chimeric gene encoding the toxin protein of B.t. a NcoI site is introduced at the translational initiation codon (ATG) of the DNA encoding the B.t. toxin such that the ATG codon is contained within the NcoI recognition site (CCATGG). DNA sequence analysis of the region of the toxin gene around the initiator codon revealed the sequence:

5'-GAGATGGAGGTAACTTATGGATAACAATCCGA-3'

MetAspAsnAsnPro

Figure 3:
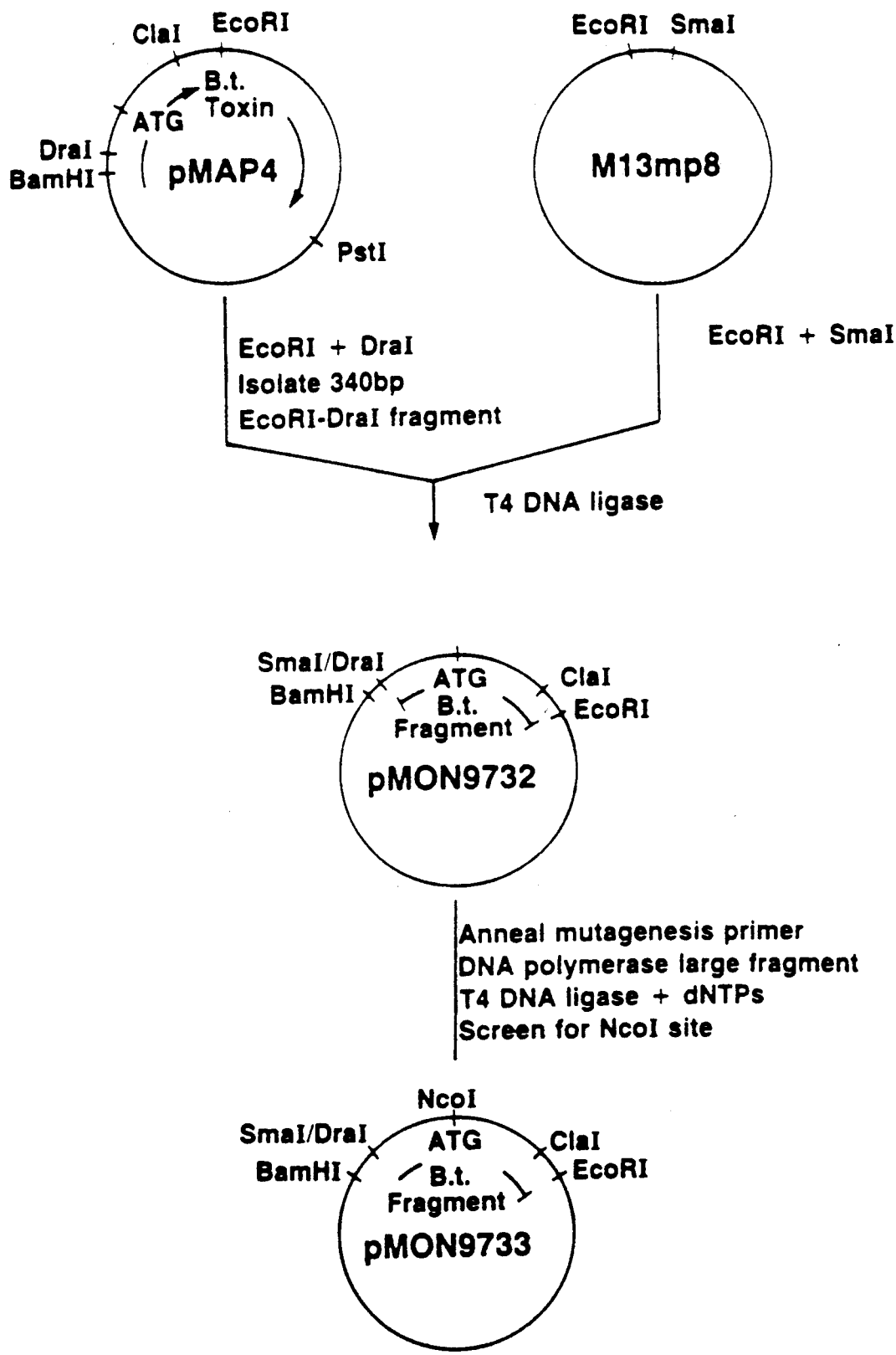
FIG. 3 shows the steps involved in the preparation of pMON9732 and pMON9733.

To introduce the desired NcoI site, it was necessary to change the sequence around the ATG from TTATGG to CCATGG. Referring to FIG. 3, a 340 bp DraI-EcoRI fragment which includes the translational initiation region was sub-cloned from pMAP4 between the SmaI and EcoRI sites of the filamentous bacteriophage vector M14mp8. This plasmid was named pMON9732. Single-stranded phage DNA from this construct contains the noncoding strand of the toxin gene sequence.

Site-specific mutagenesis was performed on single-stranded DNA from this construct by the method of Zoller and Smith (1983, *Methods Enzymol.* 100:468-500) utilizing as a primer a synthetic oligonucleotide of the sequence:

5'-GAGATGGAGGTAACCCATGGATAACAATCC-3'

Following mutagenesis a clone containing the desired change was identified by digestion of NcoI, and the presence of the NcoI site was confirmed by DNA sequence analysis. This clone was designated pMON9733.

Figure 4:
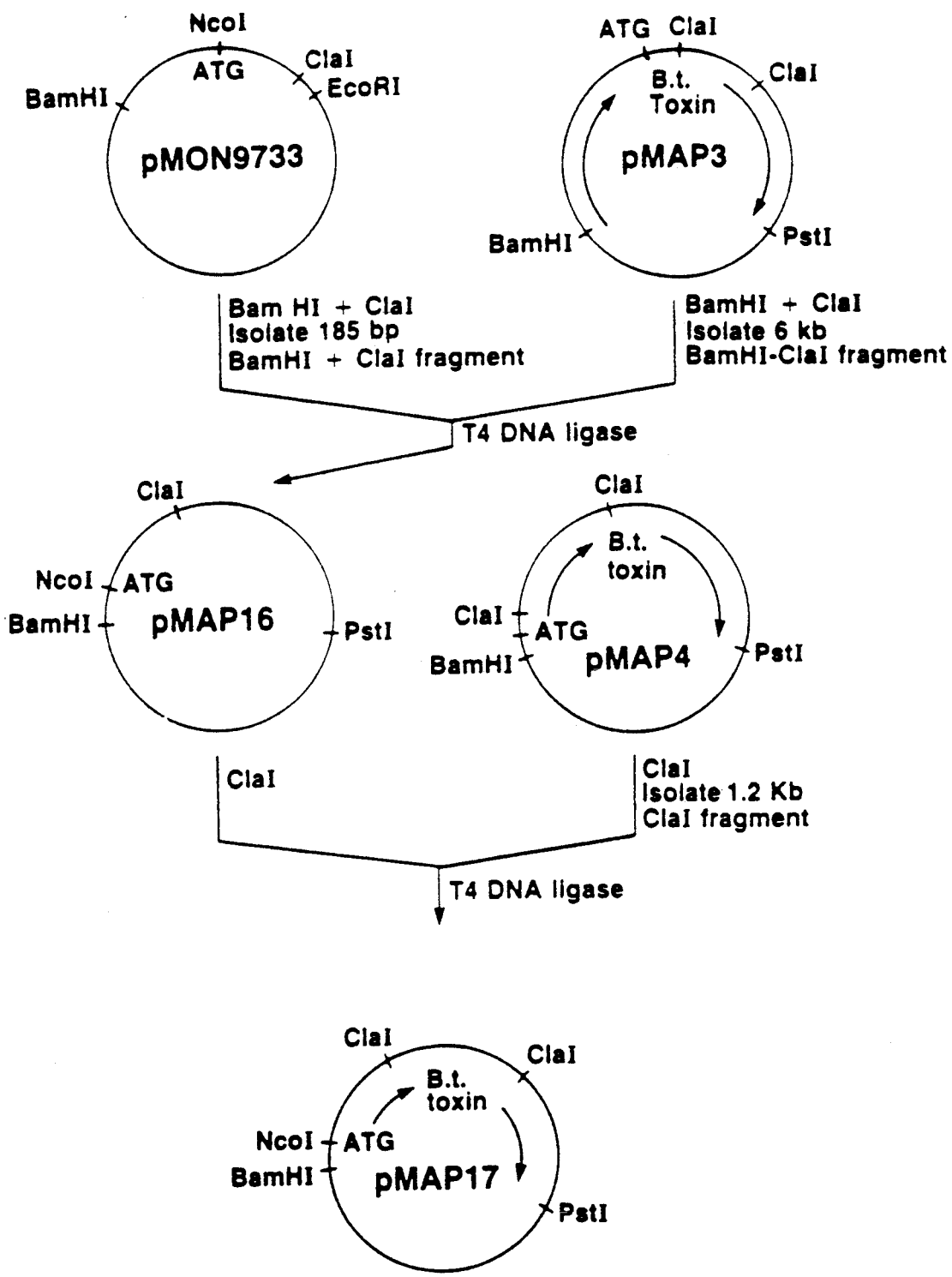
FIG. 4 shows the steps involved in the preparation of pMAP17.

An intact toxin gene was constructed which incorporated the NcoI site from the site-specific mutagenesis described above. Referring to FIG. 4, pMAP3 was digested with BamHI and ClaI and a fragment containing the pUC8 vector and the toxin gene from the ClaI site at position 1283 to the PstI site beyond the end of the gene was isolated. A 185 bp fragment extending from the BamHI site was in the mp8 multi-linker to the ClaI site at position 106 was isolated from pMON9733. These two fragments were ligated to create pMAP16. pMAP16 contains the NcoI site at the ATG but is missing the segment of the toxin gene between the ClaI sites at 106 and 1283. This ClaI fragment was isolated from pMAP4 and ligated with ClaI digested pMAP16. A plasmid containing this inserted ClaI fragment in the proper orientation to reconstruct a functional toxin gene was identified and designated pMAP17. *E. coli* containing this plasmid produced a protein of about 134,000 daltons which reacted with antibodies prepared against purified crystal toxin protein from *Bacillus thuringiensis* subspecies *kurstaki* HD-1 at levels comparable to those produced by *E. coli* containing pMAP4. coli containing pMAP17 were toxic to the Lepidopteran larvae *Manduca sexta*.

Figure 5:
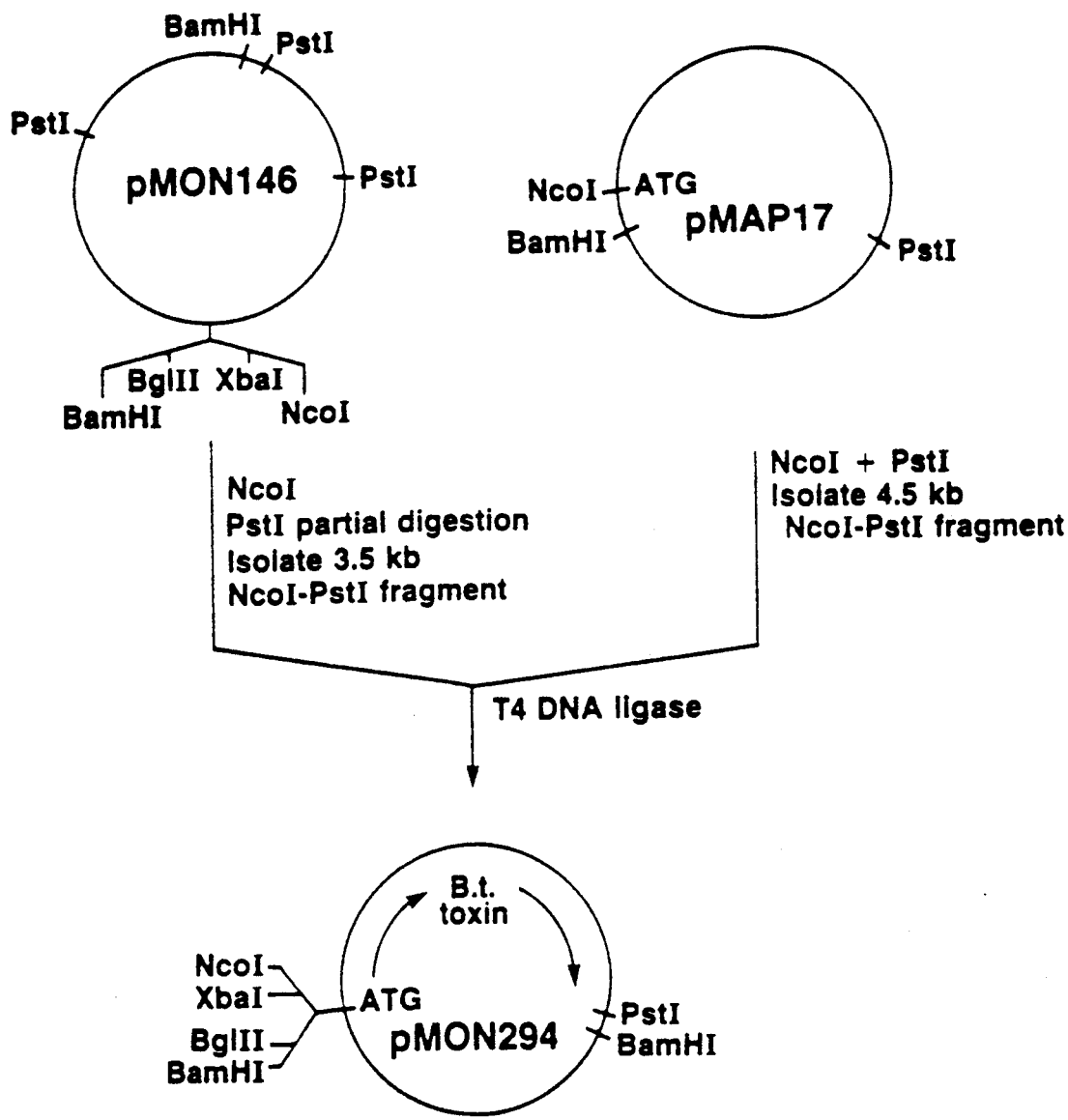
FIG. 5 shows the steps involved in the preparation of pMON294.
Figure 6:
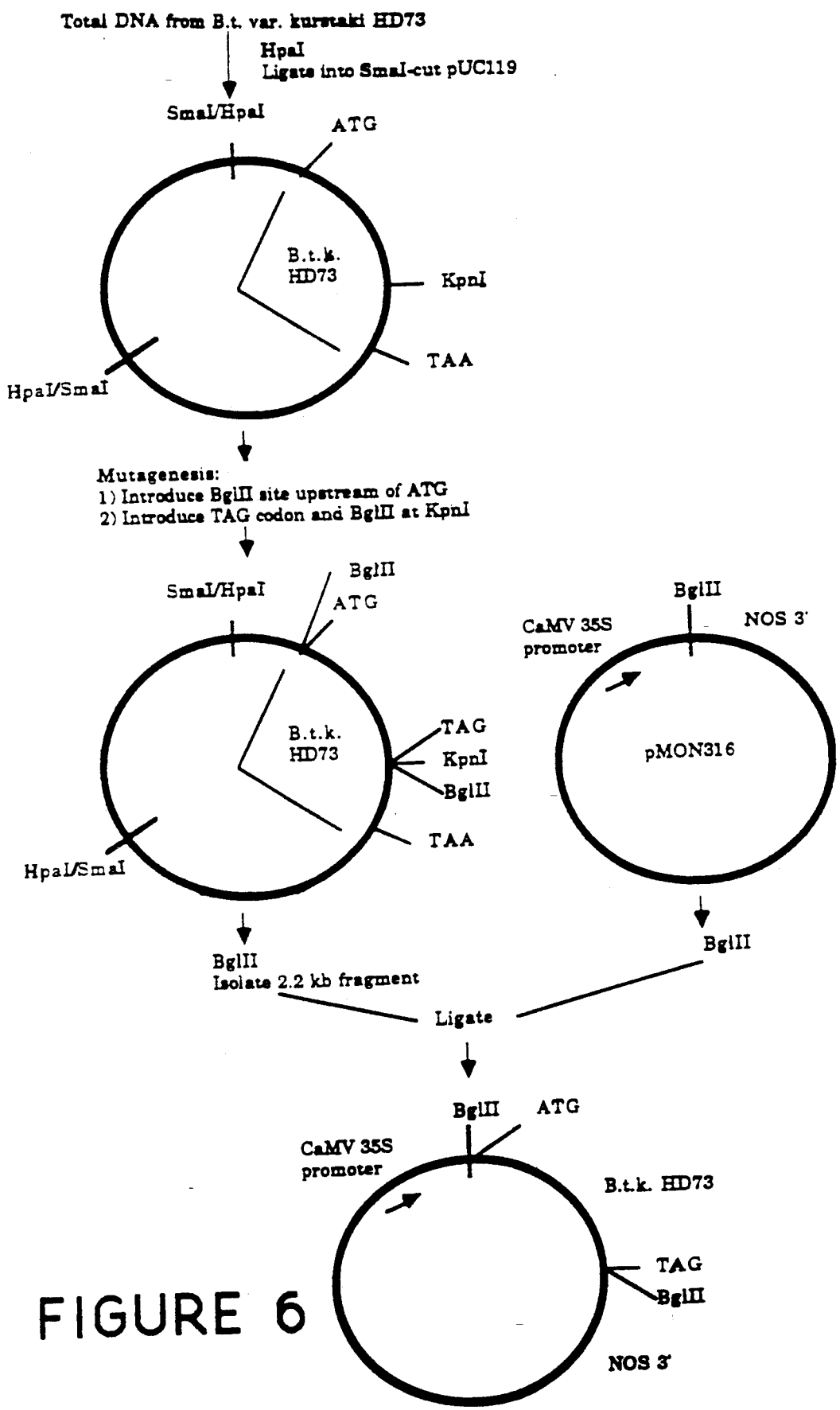
FIG. 6 shows the steps involved in the preparation of a plant transformation vector containing a gene encoding the toxin protein of B.t.k. HD-73.

To facilitate construction of chimeric toxin genes in plant transformation vectors, BamHI and BglII sites were introduced just upstream of the NcoI site in the toxin gene. Referring to FIG. 5, plasmid pMON146 was used as a source of a synthetic linker containing restriction sites for BamHI, BglII, XbaI and NcoI as shown:

5'-GGATCCAGATCTGTTGTAAGGAGTCTAGACCATGGATC-3'

BamHI BglII            XbaI NcoI pMON146 was partially digested with PstI and then digested to completion with NcoI, and a 3.5 Kb NcoIPstI fragment was isolated. The 4.5 kb NcoI-PstI fragment containing the entire toxin gene was isolated from pMAP17, and this fragment was ligated with the 3.5 kb pMON146 fragment. A plasmid containing these two fragments was designated pMON294. In pMON294 a BamHI and a BglII site are just upstream of the initiation codon for the toxin protein, and a BamHI site is just downstream of the PstI site.

A plasmid was constructed for the expression of the B.t. toxin gene in plants by ligating the 4.5 kb Ba m Hi fragment containing the toxin gene from pMON294 into pMON316 which had been digested with BglII. A plasmid which contained the toxin gene oriented such that the translational initiator was adjacent to the CaMV35S promoter was identified by digestion with EcoRI and designated pMON8053. Another chimeric plant gene was prepared comprising the full-length construct in which the structural coding sequence for the toxin was truncated at the DraI site at position 3479. This site is 10 nucleotides beyond the translational terminator codon for the coding sequence for the full-length coding sequence but very little 3' flanking sequence from the B.t. subspecies *kurstaki* gene. This construct was designated pMON9712.

Plasmid pMON9712 was prepared by digesting pMON294 with endonuclease DraI. A pair of complementary oligonucleotides having the following sequence were synthesized:

5'-TAGTAGGTAGCTAGCCA-3'

3'-ATCATCCATCGATCGGTCTAG-5'

When annealed to one another these oligonucleotides encode translational terminators in all three reading frames. The annealed oligonucleotide pair is flush ended at one end and provides a four nucleotide single-stranded region capable of ligation to BglII digested DNA at the other end. The oligonucleotides were annealed to one another and ligated to pMON294 DNA which had been digested with DraI. The ligated DNA was digested with BglII, and a BglII fragment of approximately 3.5 kb containing the desired toxin coding sequence was isolated. This fragment extends from the BglII site just upstream of the translational initiation codon to the BglII site created by the oligonucleotide pair. This BglII fragment was ligated with BglII digested pMON316. A clone (pMON9712) was identified in which the translational initiator for the toxin gene was adjacent to the 35S promoter by digestion with EcoRI.

Previous work has shown that a fragment of the B.t. toxin coding sequence which extends from upstream of the translational initiator to the Kpnl site at position 2170 produced a protein which is toxic to *M. sexta* when expressed in *E. coli.* A plant expression vector incorporating such a truncated B.t. toxin encoding gene was constructed as follows. Based on the DNA sequence of the toxin gene at the KpnI site at position 2170, a pair of complementary oligonucleotides was synthesized as shown below which when annealed to one another and ligated to the toxin gene at the KpnI site would encode two translational termination codons in frame with the toxin coding sequence.

5'-CTAGTAAA-3'

3'-CATGGATCATTTCTAG-5'

The annealed oligonucleotides provide, at one end, a four nucleotide single-stranded region capable of ligation to KpnI digested toxin gene, and, at the other end, a four nucleotide single-stranded region capable of ligation with BglII digested DNA. The oligonucleotides were annealed to one another and ligated with pMON294 which had been digested with KpnI. This ligated DNA was then digested with BglII and a 2.2 kb BglII fragment was isolated. This fragment extends from the BglII site just upstream of the translational initiator of the toxin gene to the BglII site created by the oligonucleotide pair.

A plasmid was constructed for the expression in plants of the toxin gene truncated at the KpnI site by ligating the 2.2 kb B91II fragment with BglII digested pMON316. A clone was identified by digestion with EcoRI in which the translational initiator for the toxin gene was adjacent to the CaMV35S promoter and was designated pMON9711.

(ii) B.t. *kurstaki* HD-73

A plant gene encoding the toxin of B.t.k. HD-73 is prepared in a manner analogous to the procedure described above. Referring to FIG. 6, DNA is isolated from B.t.k. HD-73, cut with Hpal and ligated into SmaI cut pUC119. Site-directed mutagenesis is employed to introduce a BglII site upstream of the start codon (ATG). A stop codon (TAG) and BglII site is introduced at the KpnI site of the toxin coding sequence.

ARTIFICIAL DIET FOR INSECT ASSAYS

The diet components (Marrone et al., 1985, *J. Econ. Entomol.* 78:290–293) are listed below in Table 1. De to the incorporation of test samples directly into the diet, 20% of the water complement has been deleted. Once prepared, the diet is poured into 500 ml squeeze bottles stored in a 40° C. water bath. Protein toxin solutions were prepared the day of the test. Typically, a 4 ml toxin solution contained in a 50 ml conical centrifuge tube was blended with 16 ml of artificial diet. After thorough homogenation, one ml of sample is promptly dispensed into each well before it hardened. After a 96-well tray was complete, it was left to dry under the vertical flow hood. One insect was added to each well, typically 16 larvae per treatment.

TABLE 1

ARTIFICIAL DIET MEDIUM

| Ingredient | Amount |
|---|---|
| Phytagar | 14.48 g |
| Deionized water | 840 ml |
| Raw Wheat Germ (ground) | 27.48 g |
| D-sucrose | 38.50 g |
| Vitamin-free casein | 32.25 g |
| Alphacel | 13.75 g |
| Salt mix w | 9.25 g |
| Methyl paraben | 0.60–1.0 g |
| Sorbic acid | 0.38–0.64 g |
| Cholesterol | 0.06 g |

TABLE 1-continued

| ARTIFICIAL DIET MEDIUM | |
|---|---|
| Ingredient | Amount |
| Raw linseed oil | 0.40 ml |
| Streptomycin | 0.064 g |
| Chlorotetracycline | 0.064 g |
| Vanderzants vitamin mix | 9.0 g |
| 10% KOH | 8.5 ml |
| Formalin (37.7%) | 1.0 ml |

INSECT TOXICITY ASSAYS (i) Lepidopteran-type Toxin Activity

Figure 10:
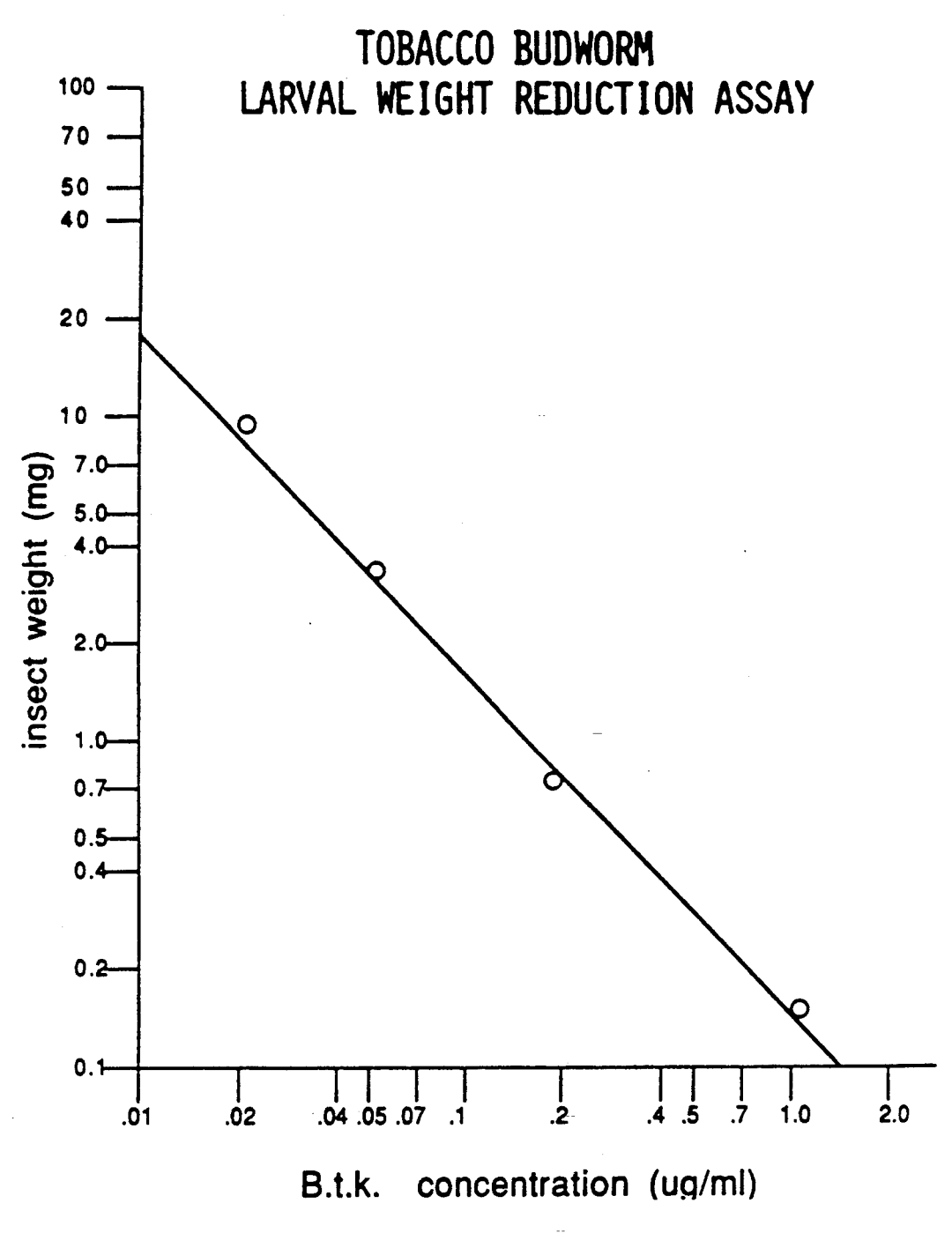

Lepidopteran toxin activity (B.t.k. HD-73 and HD-1) was assayed using newly hatched tobacco budworm (TBW) larvae in the artificial diet assay described above. TBW eggs were surfaced sterilized with 1% Clorox for 5 minutes, 0.25% peracetic acid for 2 minutes and incubated on filter paper disks placed at 25° C., 80% relative humidity for 5-6 days until hatching occurs. The diet medium was prepared and 1 ml dispensed into 16 wells. One neonate larvae was placed with a paint brush in a well, the trays sealed with MYLAR (DuPont Co.) using a heated tacking iron. One hole was poked in each well with a sterile probe for ventilation. Six days later the percentage corrected mortality was computed using Abbott's formula (Abbott, W.S., 1925, J. Econ. Entomol. 18: 265-267). For experiments where the B.t.k. efficacy was determined in terms of reduced insect larval weight, larvae at day 7, within each treatment were weighed on an analytical balance. The average weight per insect was calculated and compared to a standard curve generated with toxin protein alone (FIG. 10).

(ii) Coleopteran-type Toxin Activity

Coleopteran toxin activity was assayed using newly hatched Colorado potato beetle (*Leptinotarsa decemlineata*) larvae in a tomato leaf feeding assay. Samples of B.t.t. alone, purified seed inhibitor alone or combinations of the two proteins were prepared on the day of the test. Tween-20 (0.3%) was added and approximately 0.5 ml of sample painted onto a tomato leaf placed into a 9cm petri dish lined with moist filter paper. Ten Colorado potato beetle larvae were added to each leaf. After four days, the percentage of corrected mortality (percentage of insects alive in the control) was computed using Abbott's formula. Assays were performed in duplicate and the data combined.

EXAMPLES

[Trypsin inhibitors from numerous sources were used to potentiate the activity of Lepidopteran-type B.t. toxins isolated from B.t.t. HD-1 and B.t.k. HD-73. The inhibitor was added in varying concentrations to the above-described artificial diet which contained the B.t. toxin at levels which alone causes only minimal mortality. The purified trypsin inhibitors increase the toxic effect of the Lepidopterantype toxin against the tobacco budworm by 2 to 10 fold in the above-described diet incorporation assay. The toxic effect is observed as either an increase in mortality or a decrease in insect larval weight. The potentiating effect is observed at very low protease inhibitor concentrations (0.000003-0.03 mg/ml or $2.0 \times 10^{-6} - 2.0 \times 10^{-2}$ wt% of the diet), far below the reported insecticidal level (2-5 wt% of the diet) for the trypsin inhibitor alone

EXAMPLE 1

Figure 8:
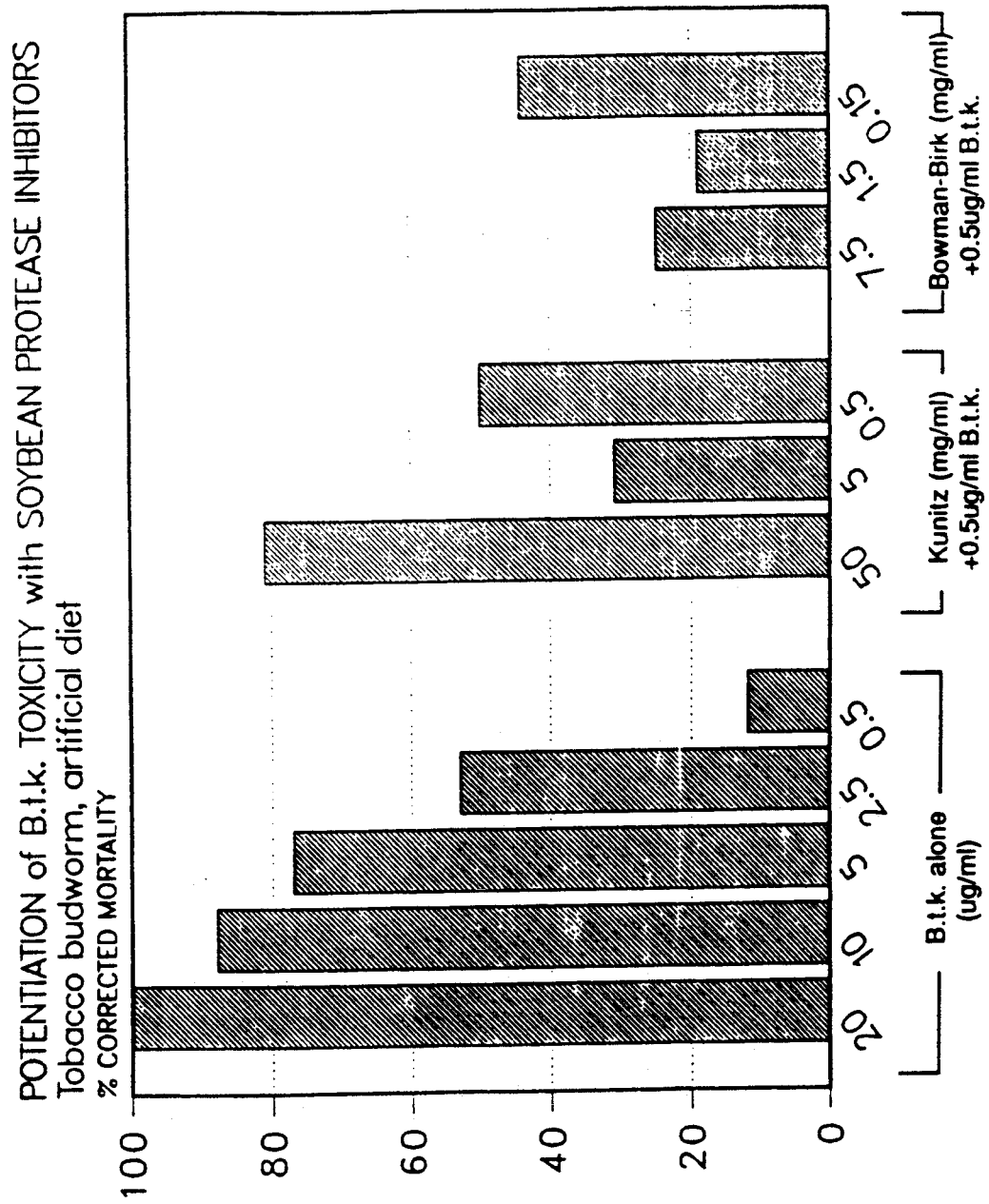
FIG. 8 illustrates the potentiation of B.t.k. HD-73 by trypsin inhibitors of soybean.

The potentiation of B.t. *kurstaki* HD-73 activity toward tobacco budworm by soybean trypsin inhibitor is represented in FIG. 8. The B.t. toxin was isolated, activated by proteolytic cleavage of the gut juices of cabbage looper *Trichopulsia ni* and incorporated into the artificial diet assay at various concentrations. A concentration was selected (0.5 µg/ml) which caused only slight mortality for use in the potentiation studies. The 0.5 µg/ml of B.t. toxin was supplemented with various concentrations of soybean trypsin inhibitor (Kunitz and Bowman-Birk). The values shown are the averages for several experiments. Overall, the trypsin inhibitors potentiated the activity of B.t.k. HD-73 from 1.5 to 8 fold.

EXAMPLE 2

The potentiation of B.t. *tenebrionis* activity toward Colorado potato beetle by soybean trypsin inhibitor (Kunitz) is represented by FIG. 9. The B.t.t. toxin was isolated and incorporated into the leaf assay at various concentrations. A concentration was selected (2.5 µg/ml) which causes only slight mortality for use in the potentiation studies. The 2.5 µg/ml of B.t.t. toxin was supplemented with various concentrations of soybean trypsin inhibitor (Kunitz-type). The value shown are the averages for several experiments. Overall, the Kunitz-type soybean trypsin inhibitor potentiated the activity of B.t.t. from 2 to 10 fold.

EXAMPLE 3

FIG. 10 shows the standard curve for tobacco budworm larval weight versus B.t.t. toxin. A potentiation study was conducted using both HD-73 and HD-1. The HD-73 toxin assayed was either full-length protoxin, a truncated protein product (~80 Kd) or the activated (*Trichoplusia ni* digested) HD-73 toxin. The HD-1 toxin assayed was either full-length protoxin or tryptic digested toxin. The toxins were potentiated by addition of various concentrations of Kunitz or Bowman-Birk soybean trypsin inhibitor which alone produced minimal larval weight reduction. The potentiation effect was averaged for the inhibitor concentrations and is summarized in Table 2 below. The potentiation effect observed varied from 1.3 to over 4.2 fold.

TABLE 2
POTENTIATION OF B.t.k. ACTIVITY
Larval Weight Reduction Assay

| | | Fold Enhancement | |
|---|---|---|---|
| B.t.k. Protein | B.t. µg/ml | Bowman-* Birk | Kunitz* |
| HD-73 (full length) | 1 | 1.4 | 2.8 |
| HD-73 (truncated) | 0.1 | 4.2 | 3.9 |
| HD-73 (T.ni.) | 0.1 | 3.3 | 3.9 |
| HD-1 (full length) | 1 | 1.3 | 2.5 |
| HD-1 (tryptic) | 0.02 | 3.2 | 3.3 |

*4.0 µM concentration

EXAMPLE 4

Using the procedure described in Example 3, the potentiation of B.t.k. HD-73 by the trypsin inhibitors of soybean was studied at various inhibitor concentrations. The final concentration of activated (*Trichoplusia ni* digested) HD-73 toxin was approximately 0.02 µg/ml. The results shown in Table 3 below are averages for 3-4 experiments for each inhibitor concentration.

TABLE 3

POTENTIATION OF HD-73 ACTIVITY WITH TRYPSIN INHIBITORS OF SOYBEAN

| INHIBITOR CONCENTRATION | FOLD INCREASE OF ACTIVITY |
|---|---|
| Bowman-Birk | |
| 0.4 μM (0.002%) | 8.2 |
| 0.04 μM (0.0002%) | 6.9 |
| 0.004 μM (0.00002%) | 3.8 |
| 0.0004 μM (0.000002%) | 2.8 |
| Kunitz | |
| 0.4 μM (0.006%) | 6.2 |
| 0.04 μM (0.0006%) | 6.2 |
| 0.004 μM (0.00006%) | 4.2 |
| 0.0004 μM (0.000006%) | 3.5 |

EXAMPLE 5

Using the procedure described in Example 3, the potentiation of B.t.k. HD-73 by partially purified or purified trypsin inhibitors from various sources was demonstrated. The final concentration of activated (*Trichoplusia ni* digested) HD-73 toxin was approximately 0.02 μg/ml. Inhibitors were isolated from sources including redbean, cowpea, squash, pancreatic tissue and soybean. The inhibitor activity was adjusted, based on chromogenic activity, such that the inhibitor activity was the same for all samples although the specific activity was not determined. The potentiation effect varied between about 2 and 4 fold. The results are shown in Table 4 below.

TABLE 4

POTENTIATION OF HD-73 WITH VARIOUS INHIBITORS

| INHIBITOR SOURCE | FOLD INCREASE OF ACTIVITY |
|---|---|
| Redbean | 2.4 |
| Cowpea | 1.8 |
| Squash | 3.3 |
| Pancreatic | 3.4 |
| Ovomucoid | 2.2 |
| Soybean Bowman-Birk | 3.3 |
| Soybean Kunitz | 3.9 |

EXAMPLE 6

Trypsin inhibitors were extracted from numerous seed sources. Crude inhibitor extracts were prepared from 1 gm seed in 5 ml of buffer as previously described and were not purified further. The crude seed extracts were used to potentiate the toxicity of both B.t.k. HD-73 (tobacco budworm) and B.t.k. (Colorado potato beetle) in the assay described above in which mortality was measured. The potentiation results are shown in FIG. 11. In all cases the crude inhibitor extract potentiated the activity of the B.t.t. and B.t.k. toxins.

EXAMPLE 7

The activity of a commercially available B.t. toxin formulation sold under the tradename DIPEL ® (Abbott Labs, Chicago, Ill.) was potentiated using the Kunitz and Bowman-Birk trypsin inhibitors of soybean. The DIPEL was added to a final concentration of 20 μg/ml of artificial diet which caused minimal larval weight reduction. The trypsin inhibitor was added to a final concentration of 0.37 mg/ml (0.2%) for the Bowman-Birk type trypsin inhibitor and 0.1 mg/ml (0.6%) for the Kunitz type trypsin inhibitor. The presence of the inhibitor potentiated the activity of DIPEL to tobacco budworm about 2.3 and 3.2 fold, respectively.

What is claimed is:

1. A composition comprising a toxin protein of a *Bacillus thuringiensis* bacteria, which toxin protein exhibits toxicity to Lepidopteran or Coleopteran insects, and a potentiating amount of a trypsin inhibitor which amount of inhibitor is between about 0.000002 and 2.0 weight percent of the composition and the molar ratio of inhibitor to toxin is in the range of about 1/1 to 104/1.

2. The composition of claim 1 in which the amount of inhibitor is between about 0.00002 and 0.02 weight percent of the composition.

3. The composition of claim 1 in which the toxin protein is from a source selected from the group consisting of *B.t. Kurstaki* HD-1, *B.t. kurstaki* HD-73, *B.t. sotto, B.t. berliner, B.t. thuringiensis, B.t. tolworthi, B.t. dendrolimus, B.t. alesti, B.t. gallaeriae, B.t. aizawai* and *B.t. subtoxicus, B.t. israeliensis, B.t. tenebrionis* and *B.t. san diego*.

4. The composition of claim 1 in which the trypsin inhibitor is from a source selected from the group consisting of pea, cowpea, split pea, lentil bean, pinto bean, lima bean, mung bean, mustard bean, soybean, red bean, caraway, cajun pea, rice, cotton, corn, wheat, sorghum, rapseed, millet, barley and squash.

* * * * *